United States Patent
Feldman (12)

(10) Patent No.: US 6,221,851 B1
(45) Date of Patent: *Apr. 24, 2001

(54) PHARMACEUTICAL THERAPY FOR CONGESTIVE HEART FAILURE

(76) Inventor: Arthur M. Feldman, 140 Riding Trail La., Pittsburgh, PA (US) 15215

( * ) Notice: Subject to any disclaimer, the term of this patent is extended or adjusted under 35 U.S.C. 154(b) by 0 days.

This patent is subject to a terminal disclaimer.

(21) Appl. No.: 09/454,569

(22) Filed: Dec. 7, 1999

Related U.S. Application Data

(63) Continuation of application No. 08/933,410, filed on Sep. 19, 1997, now Pat. No. 5,998,386.

(51) Int. Cl.[7] .................................................. A61K 31/70

(52) U.S. Cl. .............................. 514/46; 514/44; 514/47; 536/27.6; 536/27.61; 536/27.62; 536/27.63; 424/93.21; 435/455

(58) Field of Search ............................. 536/27.6, 27.61, 536/27.62, 27.63; 514/46, 47, 44; 424/93.21; 435/455

(56) References Cited

U.S. PATENT DOCUMENTS

| | | | |
|---|---|---|---|
| 5,070,877 | * 12/1991 | Mohiuddin et al. | 128/653.4 |
| 5,104,859 | * 4/1992 | Sollevi | 514/46 |
| 5,208,240 | * 5/1993 | Peet et al. | 514/263 |
| 5,219,740 | * 6/1993 | Miller et al. | 435/69.6 |
| 5,231,086 | * 7/1993 | Sollevi | 514/46 |
| 5,264,220 | 11/1993 | Long, Jr. et al. | 424/450 |
| 5,331,094 | 7/1994 | Eppler et al. | 530/395 |
| 5,391,376 | 2/1995 | Long, Jr. et al. | 424/450 |
| 5,449,522 | 9/1995 | Hill | 424/722 |
| 5,449,665 | * 9/1995 | Sollevi | 514/46 |
| 5,498,613 | 3/1996 | Rodgers et al. | 514/258 |
| 5,516,894 | * 5/1996 | Reppert | 530/350 |
| 5,521,291 | 5/1996 | Curiel et al. | 530/391.7 |
| 5,534,504 | * 7/1996 | Sollevi | 514/46 |
| 5,536,241 | 7/1996 | Zapol | 128/200.14 |
| 5,547,932 | 8/1996 | Curiel et al. | 435/85 |
| 5,550,132 | 8/1996 | Benson et al. | 514/269 |
| 5,570,683 | 11/1996 | Zapol | 604/23 |
| 5,587,300 | 12/1996 | Malter | 435/69.1 |
| 5,624,913 | 4/1997 | Proctor et al. | 514/47 |
| 5,629,298 | 5/1997 | Dobson, Jr. | 514/45 |
| 5,631,258 | 5/1997 | Borcherding et al. | 514/261 |
| 5,648,341 | 7/1997 | Sollevi . | |
| 5,705,491 | * 1/1998 | Yamada | 514/46 |
| 5,731,296 | * 3/1998 | Sollevi | 514/46 |
| 5,989,822 | * 11/1999 | Tang et al. | 435/6 |
| 5,998,386 | * 12/1999 | Feldman | 514/46 |

FOREIGN PATENT DOCUMENTS

| | | |
|---|---|---|
| 2174040 | * 10/1997 | (CA) . |
| 9402605 | * 2/1994 | (WO) . |
| 9640195 | * 12/1996 | (WO) . |
| 9850542 | * 12/1998 | (WO) . |
| 9854298 | * 12/1998 | (WO) . |
| 9913721 | * 3/1999 | (WO) . |

OTHER PUBLICATIONS

Liang and Jacobson, "A Physiological Role of the Adenosine $A_3$ Receptor: Sustained Cardioprotection," *Proceedings National Academy of Sciences USA*, 95(12), 6995–6999 (Jun. 9, 1998).*

Strickler et al., "Direct Preconditioning of Cultured Chick Ventricular Myocytes—Novel Functional of Cardiac Adenosine $A_{2a}$ and $A_3$ Receptors," *Journal f Clinical Investigations*, 98(8), 1773–1779 (Oct. 15, 1996).*

Liang, "Direct Preconditioning of Cardiac Ventricular Myocytes Via Adenosine A1 Receptor and KATP Channel," *American Journal of Physiology: Heart and Circulatory Physiology*, 40(5), H1769–H1777 (Nov., 1996).*

Stambaugh et al., "A Novel Cardioprotective Function of Adenosine A1 and A3 Receptors During Prolonged Simulated Ischemia," *American Journal of Physiology: Heart and Circulatory Physiology*, 42(1), H501–H505 (Jul., 1997).*

Dobson, JG. Jr. et al. Adenosine $A_2$ Receptor Function In Rat Ventricular Myocytes. Cardiovascular Res. vol. 34. pp. 337–347. 1997.

MacGowan, G.A. et al. Circulating Interleukin–6 In Sever Heart Failure. Am. J. Cardiol. vol. 79. pp. 1128–1131. Apr. 15, 1997.

Satoh, M. et al. Inducible Nitric Oxide Synthase and Tumor Necrosis Factor–Alpha in Myocardium in Human Dilated Cardiomyopathy. JACC. vol. 29, No. 4 pp. 716–724. Mar. 15, 1997.

Kubota, T. et al. Cardiac–Specific Overexpression of Tumor Necrosis Factor–Alpha Causes Lethal Myocarditis in Transgenic Mice. Journal of Cardiac Failure, vol. 3, No. 2, pp. 117–124. 1997 (in Press).

Bisognano J.D. et al. Preliminary Characterization of a Transgenic Mouse Overexpressing the Human β1 Adrenergic Receptor. (Abstract only). J. Invest. Med. vol. 45. p. 210A. 1997.

(List continued on next page.)

*Primary Examiner*—Gary Geist
*Assistant Examiner*—L Eric Crane
(74) *Attorney, Agent, or Firm*—Barnes & Thornburg

(57) ABSTRACT

The present invention is directed to reduce elevated levels of tumor necrosis factor-alpha (TNF-α) found in a failing heart. The present invention is directed to a composition and method of regulating TNF-α expression in myocardial tissue by treating the myocardial tissue with biological equivalents of endogenous adenosine. A composition and method of using the composition to treat patients with damaged myocardial tissue is provided which increases the cellular availability of adenosine with a resulting decrease of TNF-α levels in the heart. The present invention provides a novel pharmacological intervention program in failing mammalian hearts, and more particularly provides a cardioprotective treatment to patients with congestive heart failure.

35 Claims, 31 Drawing Sheets

OTHER PUBLICATIONS

Bozhurt, B. et al. Chronically Elevated Levels of TNF–alpha Produce Changes in LV Structure (Remodeling) and Function That Mimic the Heart Failure Phenotype. (Abstract only) Circulation. vol. 94 No. 8 (Suppl. I). p. I–662. Oct. 15, 1996.

Sajjadi, F.G. et al. Inhibition of TNF–$\alpha$ Expression by Adenosine. Role of $A_3$ Adenosine Receptors. J. Immunol. vol. 156. pp. 3435–3442. 1996.

Loh, E. et al. A Previously Unrecognized Disease Modifying Locus Associated with Increased Survival in Patients With Advanced Heart Failure. (Abstract only) Circulation. vol. 94(Suppl. I). p. I–434. 1996.

Liang, B.T. A New Cyclic AMP–Independent. $G_s$–Mediated Stimulatory Mechanism Via the Adenosine $A_{2a}$ Receptor in the Intact Cardiac Cell. J. Biol. Chem. vol. 271. No. 31 pp. 18678–18685. Aug. 2, 1996.

Torre–Amione, G. et al. Proinflammatory Cytokine Levels in Patients with Depressed Left Ventricular Ejection Fraction: A Report From the Studies of Left Ventricular Dysfunction (SOLVD). JACC. vol. 27. No. 5 pp. 1201–1206. Apr. 1996.

Testa, M. et al. Circulating Levels of Cytokines and their Endogenous Modulators in Patients with Mild to Severe Congestive Heart Failure Due To Coronary Artery Disease or Hypertension. JACC. vol. 28. No. 4 pp. 964–971. Oct. 1996.

Torre–Amione, G. et al. Tumor Necrosis Factor–$\alpha$ and Tumor Necrosis Factor Receptors in the Failing Human Heart. Circulation. vol. 93. No. 4 pp. 704–711. Feb. 15, 1996.

Habib, F.M. et al. Tumor Necrosis Factor and Inducible Nitric Oxide Synthase in Dilated. Cardiomyopathy. The Lancet. vol. 347. pp. 1151–1155. Apr. 27, 1996.

Goldhaber, J.I. et al. Effects of TNF–$\alpha$ on [$Ca^{2+}$]and Contractility in Isolated Adult Rabbit Ventricular Myocytes. Am. J. Physiol. vol. 271. pp. H1449–H1455. 1996.

Stein, B. et al. Endotoxin and Cytokines Induce Direct Cardiodepressive Effects in Mammalian Cardiomyocytes Via Induction of Nitric Oxide Synthase. J. Mol. Cell. Cardiol. vol. 28. pp. 1631–1639. 1996.

Iwase, M. et al. Adverse Effects of Chronic Endogenous Sympathetic Drive Induced By Cardiac $G_{s\alpha}$ Overexpression. Circ. Res. vol. 78. No. 4 pp. 517–524. Apr. 1996.

Palmer, J.N. et al. Interleukin–1$\beta$ Induces Cardiac Myocyte Growth But Inhibits Cardiac Fibroblast Proliferation in Culture. J. Clin. Invest. vol. 95. pp. 2555–2564. Jun. 1995.

Krown, K. A. et al. TNF$\alpha$ Receptor Expression in Rat Cardiac Myocytes: TNF$\alpha$ Inhibition of L–Type $Ca^{2+}$ Current and $Ca^{2+}$ Transients. FEBS Letters. vol. 376. pp. 24–30. 1995.

Ferrari, F. et al. Tumor Necrosis Factor Soluble Receptors in Patients with Various Degrees of Congestive Heart Failure. Circulation. vol. 92. No. 6, pp. 1479–1486. Sep. 15, 1995.

Kapadia, S. et al. Tumor Necrosis Factor–$\alpha$ Gene and Protein Expression in Adult Feline Myocardium After Endotoxin Administration. J. Clin. Invest. vol. 96. pp. 1042–1052. Aug. 1995.

Torre–Amione, G. et al. Expression and Functional Significance of Tumor Necrosis Factor Receptors in Human Myocardium. Circulation. vol. 92. No. 6 pp–1487–1493. Sep. 15, 1995.

Kuznetsov, V. et al. $\beta_2$–Adrenergic Receptor Actions in Neonatal and Adult Rat Ventricular Myocytes. Circ. Res. vol. 76. No. 1 pp. 40–52. Jan. 1995.

Bouma, M. G. et al. Differential Regulatory Effects of Adenosine on Cytokine Release By Activated Human Myocytes. J. Immunol. vol. 153. pp. 4159–4168. 1994.

Wagner, D.R. et al. Influence of Polyclonal Immunoglobulins on the Polymorphonuclear Leukocyte Response to Lipopolysaccharide of Salmonella Enteritidis as Measured with Luminol–Enhanced Chemiluminescence. Infect. Immun. vol. 62. No. 10 pp. 4320–4324. Oct. 1994.

Wagner, D.R. et al. Existence and Role of Substrate Cycling Between AMP and Adenosine in Isolated Rabbit Cardiomyocytes Under Control Conditions and In ATP Depletion. Circulation. vol. 90. No. 3 pp 1343–1349. Sep. 1994.

Stein, B. et al. Pharmocological Characterization of $A_2$–Adenosine Receptors in Guinea–Pig Ventricular Cardiomyocytes. J. Mol. Cell. Cardiol. vol. 26. pp. 403–414. 1994.

Newell, C.L. et al. Interaction of Nuclear Proteins with an AP–1/CRE–like Promoter Sequence in the human TNF–$\alpha$ Gene. J. Leukoc. Biol. vol. 56. pp. 27–35. Jul. 1994.

Reinstein, L.J. et al. Suppression of Lipopolysaccaride–Stimulated Release of Tumor Necrosis Factor By Adenosine: Evidence for $A_2$ Receptors on Rat Kupffer Cells. Hepatology. vol. 19. pp. 1445–1452. Jun. 1994.

Matsumori, A. et al. Increased Circulating Cytokines in Patients with Myocarditis and Cardiomyopathy. Br. Heart J. vol. 72. pp. 561–566. 1994.

Katz, A.M. The Cardiomyopathy of Overload: An Unnatural Growth Response in the Hypertrophied Heart. Ann. Intern. Med. vol. 121. No. 5 pp. 363–371. Sep. 1, 1994.

Parmely, M.J. et al. Adenosine and a Related Carbocyclic Nucleoside Analogue Selectivity Inhibit Tumor Necrosis Factor–$\alpha$ Production and Protect Mice Against Endotoxin Challenge. J. Immunol. vol. 151. No. 1 pp. 389–396. Jul. 1, 1993.

Forman, M.B. et al. Adenosine Attenuates Reperfusion Injury Following Regional Myocardial Ischaemia. Cardiovasc. Res. vol. 27. pp. 9–17. 1993.

Sanders, V. et al. On Classification of Post–mortem Multiple Sclerosis Plaques for Neuroscientists. J. Neuroimmunol. vol. 46. pp. 207–216. 1993.

Meghji, P. et al. Effect of 5'–Deoxy–5'–Isobutylthioadenosine on Formation and Release of Adenosine From Neonatal and Adult Rat Ventricular Myocytes. Biochem. J. vol. 291. pp. 833–839. 1993.

Tucker, A.L. et al. Cloned Receptors and Cardiovascular Responses to Adenosine. Cardiovasc. Res. vol. 27. pp. 62–67. 1993.

Dutka, D.P. et al. Tumor Necrosis Factor $\alpha$ in Severe Congestive Cardiac Failure. Br. Heart J. vol. 70. pp. 141–143. 1993.

Yokoyama, T. et al. Cellular Basis For the Negative Inotropic Effect of Tumor Necrosis Factor–$\alpha$ in the Adult Mammalian Heart. J. Clin. Invest. vol. 92. pp. 2303–2312. 1993.

Pizarro, T.T. et al. Induction of TNF–$\alpha$ and TNF–$\beta$ Gene Expression in Rat Cardiac Transplants During Allograft Rejection. Transplantation. vol. 56. No. 2 pp. 399–404. Aug. 1993.

Hecht, G.M. et al. Coexistance of Sudden Cardiac Death and End–Stage Heart Failure in Familial Hypertrophic Cardiomyopathy. JACC. vol. 22. No. 2 pp. 489–497. Aug. 1993.

Ely, S.W. et al. Protective Effects of Adenosine in Myocardial Ischemia. Circulation. vol. 85. No. 3 pp. 893–904. Mar. 1992.

Cronstein, B.N. et al. Neutrophil Adherence to Endothelium is Enhanced Via Adenosine $A_{-1}$ Receptors and Inhibited Via Adenosine $A_2$ Receptors. J. Immunol. vol. 148. No. 7 pp. 2201–2206. Apr. 1, 1992.

Giroir, B.P. et al. The Tissue Distribution of Tumor Necrosis Factor Biosynthesis During Endotoxemia. J. Clin. Invest. vol. 90. pp. 693–698. 1992.

Finkel, M.S. et al. Negative Inotropic Effects of Cytokines on the Heart Mediated by Nitric Oxide. Science. vol. 257. pp. 387–389. Jul. 17, 1992.

Gavrieli, Y. et al. Identification of Programmed Cell Death in Situ Via Specific Labeling of Nuclear DNA Fragmentation. J. Cell. Biol. vol. 119. No. 3 pp. 493–501. Nov. 1992.

Ko, Y. et al. Idiopathic Hypertrophic Cardiomyopathy in Identical Twins: Morphological Heterogeneity of the Left Ventricle. Chest. vol. 102. No. 3 pp. 783–785. Sep. 1992.

Vilcek, J. et al. Tumor Necrosis Factor: New Insights Into the Molecular Mechanisms of Its Multiple Actions. J. Biol. Chem. vol. 266. No. 12 pp. 7313–7316. Apr. 25, 1991.

McMurray, J. et al. Increased Concentrations of Tumor Necrosis Factor in "Cachectic" Patients With Severe Chronic Heart Failure. Br. Heart. J. vol. 66. pp. 356–358. 1991.

Reithmann, C. et al. Tumor Necrosis Factor α Up–Regulates $G_{i\alpha}$ and $G_\beta$ Proteins and Adenylyl Cyclase Responsiveness in Rat Cardiomyocytes. European J. Pharmacol. vol. 206. pp. 53–60. 1991.

Gulick, J. et al. Isolation and Characterization of the Mouse Cardiac Myosin Heavy Chain Genes. J. Biol. Chem. vol. 266. No. 14 pp. 9180–9185. May 15, 1991.

Subramaniam, A. et al. Tissue–Specific Regulation of the α–Myosin Heavy Chain Gene Promoter in Transgenic Mice. J. Biol. Chem. vol. 266. No. 36 pp. 24613–24620. Dec. 25, 1991.

Chin, Y. et al. Lymphocyte Adhesion to Cultured Peyer's Patch High Endothelial Venule Cell is Mediated By Organ–Specific Homing Receptors and Can Be Regulated By Cytokines. J. Immunol. vol. 145. No. 11 pp. 3669–3677. Dec. 1, 1990.

Toraason, M. et al. Comparative Toxicity of Allylamine and Acrolein in Cultured Myocytes and Fibroblasts from Neonatal Rat Hearts. Toxicology. vol. 56. pp. 107–117. 1989.

Tannenbaum, C.S. et al. Lipopolysaccharide–Induced Gene Expression in Murine Peritoneal Macrophages is Selectively Suppressed by Agents that Elevate Intracellular cAMP. J. Immunol. vol. 142. No. 4 pp. 1274–1280. Feb. 15, 1989.

Tracey, K.J. et al. Cachectin/Tumor Necrosis Factor. The Lancet. vol. 1. pp. 1122–1126. May 20, 1989.

Feldman, A.M. et al. Increase of the 40,000–mol wt. Pertussis Toxin Substrate (G Protein) in the Failing Human Heart. J. Clin. Invest. vol. 82. pp. 189–197. 1988.

Gwathmey, J.K. et al. Abnormal Intracellular Calcium Handling in Myocardium from Patients with End–Stage Heart Failure. Circ. Res. vol. 61. No. 1 pp. 70–76. Jul. 1987.

Chomczynski, P. et al. Single–step Method of RNA Isolation by Acid Guanidium Thiocyanate–Phenol–Chloroform Extraction. Anal. Biochem. vol. 162. pp. 156–159. 1987.

Semon, D. et al. Nucleotide Sequence of the Murine TNF Locus, Including the TNF–α (Tumor Necrosis Factor) and TNF–β (lymphotoxin) Genes. Nucleic Acids Res. vol. 15. No. 21 pp. 9083–9084. 1987.

Caput, D. et al. Identification of a Common Nucleotide Sequence in the 3' Untranslated Region of mRNA Molecules Specifying Inflammatory Mediators. Proc. Natl. Acad. Sci. USA. vol. 83. 1670–1674. Mar. 1986.

Shaw, G. et al. A Conserved AU Sequence from the 3' Untranslated Region of GM–CSF mRNA Mediates Selective mRNA Degradation. Cell. vol. 46. pp. 659–667. Aug. 29, 1986.

Beutler, B. et al. Purification of Cachectin, a Lipoprotein Lipase–Suppressing Hormone, Secreted by Endotoxin–Induced RAW 264.7 Cells. J. Exp. Med. vol. 161. pp. 984–995. May 1985.

Fransen, L. et al. Molecular Cloning of Mouse Tumor Necrosis Factor cDNA and Its Eukaryotic Expression. Nucleic Acids Res. vol. 13. No. 12 pp. 4417–4429. 1985.

Hanley, F. et al. Direct Measurement of Left Ventricular Interstitial Adenosine. Am. J. Physiol. vol. 245. pp. H327–H335. 1983.

Cronstein, B.N. et al. Adenosine: A Physiological Modulator of Superoxide Anion Generation by Human Neutrophils. J. Exp. Med. vol. 158. pp. 1160–1177. Oct. 1983.

Samuels, H.H. et al. Depletion of L–3,5,3$^1$–triiodothyronine and L–Thyroxine in Euthyroid Calf Serum for Use in Cell Culture Studies of the Action of Thyroid Hormone. Endocrinology. vol. 105. No. 1 pp. 80–85. 1979.

Gross–Bellard, M. et al. Isolation of High–Molecular–Weight DNA From Mammalian Cells. Eur. J Biochem. vol. 36. No. 1 pp. 32–38. 1973.

* cited by examiner

|  | Cardiomyocytes | Fibroblasts |
|---|---|---|
| CONTROL | 0.4 ± 0.3 | 0.5 ± 0.5 |
| LPS | 23.4 ± 1.2 | 6.5 ± 0.7 |
| ADENOSINE | 8.2 ± 1.1 | 5.8 ± 0.2 |
| A2 agonist | 11.1 ± 1.0 | 4.1 ± 0.6 |

FIG. 11

|  | Control (n=38) | LPS (n=38) | LPS + Adenosine (n=38) |
|---|---|---|---|
| Diastolic Fluorescence ratio | 1.15±0.01 | 1.14±0.01 | 1.15±0.01 |
| Peak systolic Fluorescence ratio | 1.70±0.02 | 1.42±0.01* | 1.73±0.02# |
| Max. Amplitude of Contraction (μm) | 3.02±0.15 | 1.51±0.10* | 2.45±0.15*,# |
| Max. Speed of Contraction (μm/s) | 36.94±1.80 | 20.15±1.16* | 30.92±2.07*,# |
| Max. Speed of Relaxation (μm/s) | 25.63±1.37 | 15.39±0.86* | 21.92±1.17*,# |

Mean ± SEM, * $p \leq 0.01$ vs. control, # $p \leq 0.01$ vs. LPS, ANOVA

FIG. 12

CLINICAL DATA

| PATIENT | GENDER | AGE | CM TYPE | SURGERY | DM |
|---------|--------|-----|---------|---------|------|
| 1 | MALE | 52 | ISCHEMIC | TRANSPL. | NIDDM |
| 2 | MALE | 37 | ISCHEMIC | LVAD | - |
| 3 | MALE | 14 | DILATED | LVAD | - |
| 4 | MALE | 67 | ISCHEMIC | TRANSPL. | IDDM |
| 5 | MALE | 62 | DILATED | LVAD | - |
| 6 | MALE | 62 | DILATED | TRANSPL. | - |
| 7 | MALE | 58 | DILATED | TRANSPL. | NIDDM |

FIG. 13

ISCHEMIC vs. DILATED CARDIOMYOPATHY

| TNF (pg/ml/mg wt.) | ISCHEMIC CM (n=3) | DILATED CM (n=4) |
|---|---|---|
| CONTROL | 0.22 ± 0.09 | 0.22 ± 0.06 |
| LPS | 5.09 ± 0.72 | 1.2 ± 0.29 * |
| ADO | 2.95 ± 061# | 1.16 ± 0.26 * |
| DPMA | 0.69 ± 0.12# | 0.21 ± 0.05 *,# |
| ITU | 0.4 ± 0.1# | 0.14 ± 0.04 *,# |

* P 0.05 ISCHEMIC vs. DILATED, #p<0.05 TREATMENT vs. LPS (ANOVA)

Tissue TNF-α Protein Levels

| | TNF-α, pg/mL | |
|---|---|---|
| | TG (n=6) | WT (n=6) |
| ventricle | 361±138* | 84±30 |
| atrium | 303±46* | 31±9 |
| lung | 89±20 | 87±29 |
| liver | 169±40 | 158±46 |
| serum | <30 | <30 |

Values are expressed as mean±SD. TG indicates transgenic mice; WT, wild type controls. *$p<0.005$ vs WT.

FIG. 22

Body, Heart, and Lung Weight by Age

| | 6W | | 12W | | 24W | | Autopsy |
|---|---|---|---|---|---|---|---|
| | TG (n=6) | WT (n=9) | TG (n=8) | WT (n=9) | TG (n=9) | WT (n=10) | TG (n=16) |
| BW, g | 20.4±1.1 | 20.1±0.9 | 21.5±1.3 | 21.9±0.8 | 31.5±3.2 | 29.2±1.9 | 22.4±11.1 |
| Heart, mg | 132±9* | 105±5 | 120±11† | 106±6 | 170±19† | 142±12 | 244±128‡ |
| Heart/BW, mg/g | 6.47±0.21* | 5.24±0.30 | 5.58±0.43* | 4.81±0.17 | 5.40±0.38† | 4.85±0.24 | 11.79±4.31‡ |
| Lung/BW, mg/g | 7.02±0.20 | 7.08±0.85 | 6.76±0.57 | 6.55±0.24 | 5.44±0.69 | 5.73±0.49 | 9.01±4.80§ |

Values are expressed as mean±SD. TG indicates transgenic mice; WT, wild type controls; BW, body weight. *$p<0.001$ vs WT; †$p<0.01$ vs WT; ‡$p<0.001$ vs others; §$p<0.05$ vs others.

FIG. 23

Left Ventricular Volume and Ejection Fraction

| | 9W | | 24W | |
|---|---|---|---|---|
| | TG (n=3) | WT (n=3) | TG (n=4) | WT (n=4) |
| HR, bpm | 215±11 | 227±15 | 222±15 | 212±28 |
| EDV/BW, mm³/g | 2.42±0.29 | 2.11±0.16 | 2.63±0.42* | 2.01±0.26 |
| ESV/BW, mm³/g | 0.88±0.24 | 0.68±0.17 | 1.30±0.32* | 0.59±0.06 |
| EF | 0.64±0.06 | 0.68±0.07 | 0.51±0.10† | 0.71±0.02 |

Values are expressed as mean±SD. TG indicates transgenic mice; WT, wild type controls; HR, heart rate; BW, body weight; EDV, end-diastolic volume; ESV, end-systolic volume; EF, ejection fraction. *$p<0.05$ vs WT; †$p<0.01$ vs WT.

FIG. 24

PHARMACEUTICAL THERAPY FOR CONGESTIVE HEART FAILURE

Cross Reference to Related Applications

This application is a continuation of U.S. application Ser. No. 08/933,410, filed Sep. 19, 1997, now U.S. Pat. No. 5,998,386, issued Dec. 7, 1999.

BACKGROUND OF THE INVENTION

Nearly four million patients in the U.S. carry the diagnosis of congestive heart failure and congestive heart failure represents the most common discharge diagnosis (DRG) at hospitals across the U.S. In 1995, the Healthcare Finance Commission spent over 15 billion dollars for the care of patients with the diagnosis of CHF. Since this represented only the medicare and medicaid populations, the cost burden to the commercial insurance industry was enormous.

Congestive heart failure is not a specific disease, but rather a compilation of signs and symptoms, all of which are caused by an inability of the heart to appropriately increase cardiac output during exertion. The cardiac diseases associated with symptoms of congestive failure include dilated cadiomyopathy, restrictive/constrictive cardiomyopathy, and hypertrophyic cardiomyopathy. Although patients with all three of these diseases present with the classical symptoms of shortness of breath, edema, and overwhelming fatigue, it is clear that the vast majority of patients presenting with failure have a dilated cardiomyopathy. Therefore, "congestive heart failure" (CHF) is generally considered equivalent to a dilated cardiomyopathy. Dilated cardiomyopathy patients have typical symptoms that are caused by both systolic as well as diastolic dysfunction, although the systolic dysfunction clearly predominates. In approximately half of the patients with dilated cardiomyopathy, the cause of the heart dysfunction is ischemic heart disease due to coronary atherosclerosis. That is, patients have had either a single myocardial infarction or multiple myocardial infarctions and the resultant scarring and remodeling has resulted in the development of a dilated and hypofunctional heart. In the remaining patients, the disease is referred to as idiopathic dilated cardiomyopathy as the causative agent remains undefined. Although modest differences exist between the patient with idiopathic (IDC) and ischemic (ISC) heart failure, they both share an abysmal prognosis and excessive morbidity and mortality. Indeed, patients with congestive heart failure have a one year survival of nearly 70% and a five year survival of only 20% after referral to a tertiary heart failure center. Morbidity is also significant as the average heart failure patient is hospitalized approximately two times each year with an average length of stay of greater than five days. Approximately half of all patients with congestive failure die suddenly—presumably due to a ventricular arrhythmia and sudden death, while the remaining patients die of worsening congestive failure.

Hemodynamically, the failing human heart demonstrates systolic dysfunction but also marked diastolic dysfunction. The diastolic dysfunction is thought to be due to abnormalities in two proteins that regulate the uptake of calcium in the sarcoplasmic reticulum storage pools, phospholamban and calcium-ATPase. Another hallmark of the development of the end-stage heart failure phenotype is maladaptive remodeling that includes: 1) cellular hypertrophy; 2) apoptosis; 3) interstitial infiltrates; 4) intesstitial fibrosis; 5) dilation of the ventricular cavity with thinning of the wall of the myocardium; and 6) occasional myocytes necrosis.

Since the primary abnormality in CHF is marked systolic dysfunction, investigators presumed that an inotropic agent, i.e., a drug that increases cardiac contractility, would benefit patients with heart failure. During the late 1960's and 1970's, a group of seminal studies elucidated the primary components of excitation contraction coupling in the heart. It was recognized that the most potent means of enhancing cardiac contractility both endogenously and exogenously was adrenegic stimulation. Beta-adrenergic receptors located on the cardiac sarcolemma coupled adrenergic agonists with the effector enzyme adenylyl cyclase via the guanine nucleotide-binding regulatory proteins. When activated, adenylyl cyclase produced the intracellular second messenger cyclic AMP with resultant activation of the promiscuous cell phosphorylator, protein kinase A. Once activated by cyclic AMP, protein kinase A phosphorylated the sarcolemmal gated calcium channel, the sarcoplasmic reticulum regulatory protein phospholamban, and the contractile protein troponin. Phosphorylation of these three proteins effected enhanced contractility via increased intracellular calcium levels and enhanced relaxation via facilitated uptake of calcium in the sarcoplasmic reticulum storage pools and decreased sensitivity to calcium due to phosphorylation of troponin. The second messenger signaling pathway could be attenuated by metabolism of cyclic AMP by the enzyme phosphodiesterase or alternatively by inhibiting receptor-G protein coupling through the receptor kinase Bark. Unfortunately, neither adrenergic agonists nor phosphodiesterase inhibitors proved beneficial in patients with congestive heart failure. In fact, large randomized and placebo-controlled clinical trials demonstrated an increase in mortality in patients treated with agents that as their major mechanism of action enhanced intracellular concentrations of cyclic AMP.

A second approach to increasing contractility has been the use of agents that increase the sensitivity of the contractile proteins to calcium. However, most inotropic agents of this class have also been associated with an increase in mortality.

At present, only one oral and three intravenous inotropic agents are approved for treatment of heart failure in the U.S. Digoxin, the only oral inotrope, was shown in a large randomized, double-blind and placebo controlled trial to have a neutral effect on survival in heart failure. However, there were concerns that it might have deleterious effects in some subgroups. milrinone, amrinone and dobutamine are beneficial in the acute therapy of congestive heart failure. However, chronic therapy with oral Milrinone or amrinone was associated with a marked increase in mortality. Similarly, chronic therapy with dobutamine has also been associated with increased mortality. All three of these intravenous agents augment contractility by increasing intracellular concentrations of cyclic AMP.

Another approach to the therapy of patients with congestive heart failure was based on the recognition that patients with congestive heart failure expressed a group of neurohormonal substances whose plasma concentrations could be inversely associated with morbidity and mortality in large populations of patients with CHF. These neurohormonal agent all share a common finding: when given in vivo or in vitro they can initiate an aladaptive remodeling of the heart and in some cases are cardiotoxic. Additionally, in experimental CHF models, they delay or attenuate the development of the heart failure phenotype.

The first neurohormonal agent to successfully serve as a therapeutic target was angiotensin II potent vasoconstrictor and activator of aldosterone. In the patient with CHF, this increase in blood volume and peripheral vascular resistance augments both preload and afterload resulting in further compromise of cardiac function. Indeed, studies have shown a direct relationship between increasing levels of angiotensin II (and/or renin) and cardiovascular mortality. Interestingly, transgenic mice that over-express angiotensinogen and therefore display elevated levels of angiotensin II demonstrate hypertension but do not have a phenotype consistent with congestive heart failure. Thus, it may be their effects on activating the bradykinin pathway or even an anti-adrenergic effect that is responsible for the beneficial effects of ACE inhibitors. Although angiotensin converting enzyme inhibitors have become a mainstay of therapy in patients with CHF and have been shown to be cost effective for long-term therapy, their overall impact on CHF has actuality been very modest, approximately a 18 to 22 percent decrease in mortality over four years.

In the early 1980's, there was first demonstrated a direct relationship between increasing levels of plasma catecholamines and mortality in patients with congestive failure. The fact that high levels of circulating catecholamines had pathophysiologic consequences was demonstrated by the finding that exposure of myocytes to chronic adrenergic stimulation resulted in cardiace remodeling with development of cardiac dilation and fibrosis. In addition, adrenergic activation caused abnormalities in receptor-effector coupling in the heart that replicated biochemical changes seen in the failing human heart: 1) marked down-regulation of the beta-adrenergic receptor; 2) uncoupling of the beta 2-adrenergic receptor from adenylyl cyclase; and 3) increased activity of the inhibitory G protein. Therefore, agonist-mediated abnormalities in receptor—G protein—adenylyl cyclase coupling explained the finding that the failing human heart was markedly insensitive to adrenergic drive. In a large multi-center trial of the beta-blocker metoprolol, there was no difference in survival in patients receiving active drug as versus those receiving placebo. However, there was a significant benefit when assessing the combined end-point of either death or the need for cardiac transplantation. As would be expected with an adrenergic blocker, the use of metoprolol was associated with a significant up-regulation of myocardial beta-adrenergic receptors. More recently, a group of clinical trials have assessed the use of carvedilol, a novel beta-adrenergic antagonist having vasodilator properties. Although the survival benefits of carvedilol were greater than those seen with the angiotensin converting enzyme inhibitors, metaanalysis of the U.S. trials included only 50 events. Therefore, the exact benefits on survival remain undefined. Beta-blockers are not easy to use in patients with CHF, as they require careful up-titration and cannot be utilized as rescue therapy. Carvedilol, for example, cannot be used for rescue therapy as it requires careful up-titration over a minimum of several weeks.

Additionally, there is an ongoing clinical trial with bucindolol, an agent that is very similar to carvedilol in that it has both beta blocking and vasodilator properties. Unlike carvedilol, bucindolol effects a significant up-regulation of receptor density and may therefore more accurately represent a "beta blocker." However, beta-blockers are difficult to utilize, and their mortality benefits remain unproven.

A more recent finding is that the proinflammatory cytokines are elevated in patients with congestive heart failure. Indeed, there is a direct relationship between elevated levels of TNF-α and II-6 and the degree of hemodynamic abnormalities. Similarly, the higher the TNF-α level the more severe the heart failure symptoms. Perhaps the most intriguing finding was that TNF-α is not expressed by normal human heart but is expressed in abundant amounts by human failing heart. Furthermore, TNF-α induces the expression of the proinflammatory cytokine II-1B. Either TNF-α or II-1B can recapitulate in vitro many of the biochemical and molecular biological abnormalities that characterize the failing human heart.

One anti-cytokine strategy that has been utilized in Phase I trials for the therapy of patients with CHF is subcutaneous administration of TNF-α soluble receptors (r75). This strategy was based on the assumption that soluble receptors would soak up free TNF-α thereby decreasing the amount of ligand that was available to the endogenous cell-surface receptors. However, difinitive assessment of this therapy requires a large multi-center controlled clinical trial. However, intuitively, the use of soluble receptors has several potential limitations: 1) the receptors can only be administered intravenously or subcutaneously; 2) other cytokines, i.e., IL-1b might also play a role in the cardiac pathophysiology of the inflammatory cytokines; 3) patients receiving long-term administration of TNF-α soluble receptors might be more susceptible to infectious or malignant diseased; and 4) intracellular cytokine expression might have important autocrine effects that are over and above the paracrine effects of the cytokines secreted by the myocytes.

A second strategy to inhibit TNF-α has utilized intravenous immuroglobulin IVIG) in an open-labeled clinical trial. IVIG has multiple properties including anticytokine effects. Its use was associated with significant improvements in ejection fraction and a suggestion of improved survival.

Perhaps the most intriguing possibility for the therapy of heart failure comes from recent studies assessing the effects of adenosine on myocardial cytokine production. Adenosine, a naturally occurring nucleotide, is expressed endogenously in mammals. At physiologic concentrations, adenosine substantially inhibits the ability of neonatal rat myocytes in culture to express TNF-α in response to lipopolysaccharide (LPS). This inhibitory response can be seen when adenosine is given before, during, or up to one hour after exposure to LPS and a similar effect is appreciable in isolated adult myocytes as well as in adult rat papillary muscle preparations. Pharmacologic testing suggests that the effects of adenosine on TNF-α inhibition are mediated via the $A_2$-adenosine receptor through stimulation of cyclic AMP since $A_2$ agonists and cyclic AMP derivatives mimic but $A_2$-antagonists attenuate the anti-TNF-α effects. That adenosine-related modulation of TNF-α expression may have physiologic importance in humans comes from recent studies of cytokine expression in papillary muscle preparations isolated from failing human heart. At baseline, human hearts express abundant amounts of TNF-α. However, the level of expression can be increased as much as 10-fold by modest concentrations of LPS and this effect can be inhibited by adenosine. These anticytolcine effects would be expected to prevent the cytokine-medicated maladaptive remodeling in patients with myocardial damage and in so doing decrease the incidence of worsening heart failure and increase long-term survival.

U.S. Pat. No. 5,629,298, which is hereby incorporated herein by reference in its entirety, teaches that an $A_2$ agonist increases the contractile performance of the heart. However, this teaching does not appreciate the use of adenosine analogs as a treatment for the repair and rehabilitation of diseased or damaged myocardial tissue.

U.S. Pat. No. 5,629,298 to Dobson teaches that administration of an adenosine $A_2$ agonist, but not adenosine, can be used to increase the contractile performance of a compromised myocardium in a mammal. Dobson also attests that the use of adenosine $A_2$ agonists in conjunction with a second compound which potentiates the beneficial effect of adenosine $A_2$ receptor agonists, e.g., an adenosine transport inhibitor, an inhibitor of adenosine metabolism, or an adenosine $A_1$ receptor antagonist would be beneficial for increasing contractile performance. Dobson proposes that the beneficial effects are the result of enhanced adenylyl cyclase activity in the presence of an $A_1$ agonist. However, the basic teaching of Dobson and the rationales proposed for its use are inaccurate.

SUMMARY OF THE INVENTION

The proinflammatory cytokines are very important neurohormonal compounds that are differentially expressed in patients with CHF. The cellular amplification of the immune response is accompanied by the release of a variety of proinflammatory cytokines including interferon-y, tumor necrosis factor (TNF), interleukin-1, interleukin-2, and interleukin-6. These cytokines recruit additional lymphocytes, monocytes, and other cell types to the site of antigen recognition and promote their promotion and differentiation, with resultant amplification of the initial immune response. The role of humoral immunity in the genesis of myocyte injury remains controversial, however, chronic, immune-mediated myocardial injury has been associated with a persistence of infiltrating immune cells and factors in the myocardium. It was initially thought that the presence of active immune cells resulted in both modulation of myocyte function and remodeling of myocardial architecture. Recent studies have suggested a role for cytokines in modulating cardiac function. Indeed, the cytokine TNF has been shown to diminish myocardial function in experimental models and in humans. Recent studies have clearly demonstrated that in the adult cardiac myocyte, TNF exerts a concentration-and time-dependent negative inotropic effect that is reversible upon removal of the cytokine. Furthermore, these negative inotropic effects appeared to be the direct results of alterations in intracellular calcium homeostatis in the adult myocyte. At the clinical level, recent studies have implicated cytokine expression—and in particular, the expression of TNF—in the development of congestive heart failure. However, TNF has also been implicated in the development of a variety of cardiac diseases, including acute viral myocarditis, cardiac allograft rejection, and myocardial infarction. In patients with heart failure, high circulating cytokine levels were originally associated with cachexia and a greater incidence of hyponatremia and renal dysfunction. However, more recently it has been shown that elevated cytokines were associated with more severe hemodynamic abnormalities, worse symphony and a worse prognosis. Therefore, measurement of proinflammatory cytokine levels in patients with CHF provides a prognostic measure not different from that of angiotensin II or neurepinephrine. For over two decades, the proinflammatory cytokines have been extensively studied because of their role in mediating the inflammatory cascade. However, it has recently been observed that failing, but not non-failing myocardium re-expressed proinflammatory cytokines and that this production occurred in the myocytes themselves and did not require the presence of inflammatory cells. In addition, it has been recognized that TNF receptors could be found in the cardiac sarcolemmal membrane and that these receptors were shed into the circulation in patients with congestive failure. That TNF-α has pathophysiologic importance in the heart is evident by the fact that virtually any noxious stimuli including stretch, ischernia, or trauma can signal the myocyte to produce TNF-α. This phenomenon was recently demonstrated by the fact that modest changes in filling pressures in an isolated working heart model effected a substantial re-expression of TNF-α.

Over the past decade, investigators have identified a group of maladaptive changes that appear to be ubiquitous in the failing human heart. These include: 1) a decrease in beta adrenergic receptor density; 2) an increase in adrenergic drive; 3) uncoupling of the beta 2-adrenergic receptor from cyclic AMP stimulation; 4) adrenergic insensitivity; 5) enhanced function of the inhibitory guanine nucleotide regulatory protein; 6) re-expression of the fetal gene program including atrial natriuretic factor; 7) abnormal calcium homeostasis with delayed sarcoplasmic reticulum calcium uptake; 8) decreased expression of calcium ATPase and phospholamban; and 9) increased fibrosis with remodeling of the extracellular matrix due to abnormalities in the activities of metalloproteinases and inhibitor of metalloproteinases (TIMPS). Therefore, perhaps the most compelling data supporting the relevance of cytokine re-expression to the development of the heart failure phenotype comes from basic research studies which have demonstrated that cytokines can recapitulate many, if not most, of the biochemical and cell biological changes associated with CHF. It has been demonstrated that the proinflammatory cytokines 1LI-beta or TNF-α could attenuate the ability of myocytes to produce cyclic AMP in the presence of adrenergic stimulation. This effect appeared to be mediated by enhanced activity of the G inhibitory protein. Similarly, it was also found that when myocytes were exposed to TNF-α, calcium transients were delayed and relaxation was prolonged analogous to changes recognized in failing human heart. More recently, we have demonstrate that the proinflammatory cytokine 1LI-beta effected a substantial decrease in the expression of phospholamban and CaATP-ase in neonatal myocytes—a finding that could be replicated by treating adult rats with the proinflammatory cytokine activator LPS. Finally, we have identified three differentially expressed genes—the tyrosine kinase receptor protein REK-4, a metalloproteinases inhibitor TIMP-3, and the metalloproteinases-disintegrin ADAM. The relevance of diminished expression of REK-4 is unclear; however, it is interesting to note that the effects of the proinflammatory cytokines on the function of Gi could be attenuated by exposure to the tyrosine kinase inhibitor genestein. The potential relevance of altered expression of TIMP-3 and ADAM 10 is more obvious. Myocyte drop-out, disorganization and fibrosis are pathognomonic findings in virtually all patients with end-stage CHP. Since this remodeling would clearly require both metabolism of existing extracellular matrix as well as the laying-down of new fibrous tissue, enhanced break down by TIMP-3 and synthesis of new extracellular matrix by ADAM 10 could be imperative in the development of the heart failure phenotype. Indeed, in a recent study we have demonstrated that hearts from patients with end-stage cardiomyopathy demonstrate a significant and substantial decrease in the steady state levels of the mRNA encoding several members of the TIMP family of protease inhibitors. These changes in mRNA levels were also reflected in decreases in the amounts of the selected TIMP proteins. In contrast, ADAM 10 expression is not altered in the failing human heart; however, it is possible that other members of the ADAM family of metalloproteinases might be differentially expressed in human heart failure. It is important to note that some of the cytokine effects can be attributed to IL-1B while others are attributable to IL-6. Since the heart maker IL-6 and IL-1B in response TNF, an anti TNF strategy would inhibit expression of other cytokines as well.

Although investigators have recognized for over two decades that neurohormonal activation participates in the pathobiology of congestive failure, skeptics have continued to question whether elevated levels of these neurohormonal substances represented causative factors or merely associated epiphenomenon. Indeed, investigators have questioned the importance of TNF expression in the development of CHF despite the overwhelming in vitro data, for this reason, we took advantage of transgenic technology to create a line of mice harboring a transgene overexpressing TNF-α in a cardiac specific manner. We hypothesized that a robust expression of TNF-α was most likely to result in the development of a heart failure phenotype. Therefore, in our initial experiments, we created a construct that lacked a mRNA destabilizing region in the 3' tail of the TNF-α gene. This mutation was highly lethal as all transgenic animals died by 10 days of age, presumably due to an overwhelming myocarditis. Alternatively, a second construct containing the 3' destabilizing region was used to create a stable line of transgenic mice over-expressing TNF-α, albeit at a lower level of expression. By three months of age, the TNF-α transgenic mice demonstrate: 1) interstitial infiltrates; 2) interstitial fibrosis; 3) left ventricular hypertrophy; and 4) mild left ventricular dysfunction. By six months of age, the mice demonstrate: 1) left ventricular dilation; 2) diminished adrenergic responsiveness; 3) decreased left ventricular ejection fraction; and 4) thinning of the ventricular walls. Furthermore, fibrosis is significantly increased in the 6 month old mice. Additionally, these mice have a six month mortality of approximately 20%, consistent with that seen in patients with Class III–IV heart failure. Interestingly, the transgenic mice demonstrate cardiac re-expression of the fetal gene program that characterizes heart failure in humans and develop changes in gene expression similar to that observed in end-stage failing human heart. Similarly, the transgenic mice demonstrate frequent premature ventricular ectopy on continuous holter monitoring and a substantial number of the mice die suddenly, presumably due to an arrythmogenic event. Finally, these mice have demonstrated in vivo that TNF initiates the expression of Il-1B by the myocardium. Therefore, these transgenic recapitulate the pathology and hemodynamics associated with heart failure in humans, demonstrate ventricular remodeling that is maladaptive and disadvantageous and provide a novel platform for the evaluation of new therapeutic strategies for treating congestive failure.

OBJECTS OF THE PRESENT INVENTION

It is an object of the present invention to provide a composition and method for treating congestive heart failure which improves survival and lessens the development of worsening heart failure.

It is another object of the present invention to block the production and availability of pro-inflammatory cytokines in a failing human heart.

It is another object of the present invention to reduce levels of TNF-α in a patient with congestive heart failure.

It is another object of the present invention to decrease myocyte Il-1B levels by inhibiting TNF-α expression.

It is yet another object of the present invention to selectively activate the adenosine $A_2$ receptor in order to prevent maladaptive remodeling of the myocardium including fibrosis, apoptosis ad necrosis.

It is yet another object of the present invention to administer therapeutically effective amounts of adenosine or adenosine analogs to treat a patient having acute congestive heart failure wherein said adenosine reduces the level of TNF-α measured in programs per milliliter in the patient by preferably 10–90%, more preferably by 30–70%, and most preferably by 50%.

It is yet another object of the present invention to stimulate endogenous production of adenosine or the biological equivalent thereof utilizing agents that inhibit adenosine metabolism or gene transfer technology.

It is yet another object of the present invention to improve cardiac function in patients with acute heart failure.

It is yet another object of the present invention to decrease the incidence of sudden death in patients with CHF.

It is yet another object of the present invention to prevent the development of symptoms in patients with Class I and Class II CHF by inhibiting the re-expression of proinflammatory cytokines.

Finally, it is yet another object of the present invention to provide a transgenic mouse having the phenotypical characteristic of end stage heart failure.

These and other objects of the present invention will be apparent from the drawings and detailed description contained herein.

BRIEF DESCRIPTION OF THE DRAWINGS

FIG. 11 is a table comparing the present inventions effect between neonatal myocytes and fibroblasts. A cardiomyocyte rich preparation, containing 100,00 cells (93% cardiomyocytes) and a fibroblast rich preparation containing 100,00 cells (95% fibroblasts) were exposed to LPS 10 ng/ml (*E. coli* 0127) for 6 hours (n=3). Where indicated, adenosine 10 μmol/L or the $A_2$ agonist DPMA 10 nmol/L were added at time 0. After 6 hours, supernatants were collected and TNF-α was measured with ELISA.

FIG. 12 is a table illustrating the effect of LPS and adenosine on cellular calcium and contraction-relaxation in neonatal cardiomyocytes. Cultured neonatal myocytes were treated with diluent (control), LPS *E. coli* (100 ng/ml) and LPS plus adenosine (10 μmol/L) for 5=4 days; treatments were performed after isolation and repeated on days 2 and 4 when medium was changed. Myocytes were plated on coverslips and electrically driven (1 Hz). Intracellular calcium was measured as fura-2 fluorescence ratio and contraction-relaxation parameters were determined using video-edge detection. *p<0.01 vs. control, #P<0.01 vs. LPS (n=38, ANVOA).

FIG. 13 is a table illustrating Clinical Data. Cardiomyopathy (CM), left ventricular assist device (LVAD), diabetes mellitus (DM), non-insulin dependent DM (NIDDM), insulin dependent DM (IDDM).

FIG. 15. Ischemic vs. dilated cariomyopathay. Human heart muscle sections were stimulated with 10 μg ml LPS (*E. coli* 0127) at time 0. Where indicated, adenosine (ADO) 10 μmol/L, the A agonist DPMA 10 mmol/L or the adenosine kinase inhibitor iodotubercidin (Itu) 10 μgmo/L were added at time 0. After 4 hours, supernatants were collected and TNF-α was measured with ELISA. *p<0.05 ischemic vs. dilated, #p<0.05 treatment vs. LPS (ANOVA).

FIG. 22 is a table illustrating Tissue TNF-α protein levels.

FIG. 23 is a table illustrating body heart and lung weight of the travsglue mice.

FIG. 24 is a table illustrating left ventricular volume and ejection fraction of wild type transgenic mice.

DETAILED DESCRIPTION OF THE INVENTION

I. Introduction

Figure 1A:
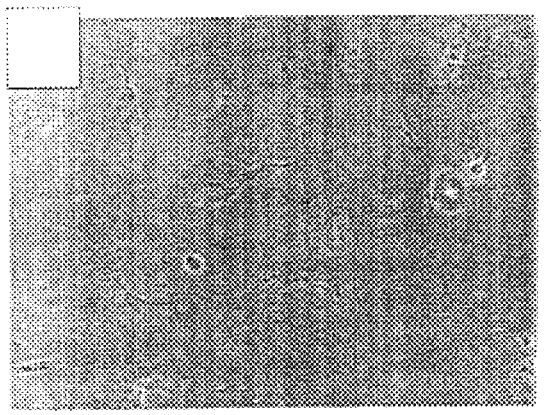
FIG. 1. Light microscopy (A,C) and immunohistochemical staining (B,D) of cultured neonatal rat cardiomyocytes with antibodies to myosin heavy chain (B) and rat TNF-α (D). The primary antibodies to myosin heavy chain and TNF-α were stained with secondary antibodies conjugated with rhodamine (red fluorescence) and fluorescein (green fluorescence), respectively. Myocytes were exposed to LPS (10 ng/ml) for 6 hours. Antimyosin labeling shows that—93% of the cells are cardiomyocytes. Note that cells stain positive for TNF-α in the presence of LPS. Magnification× 400.
Figure 1B:
Figure 1C:
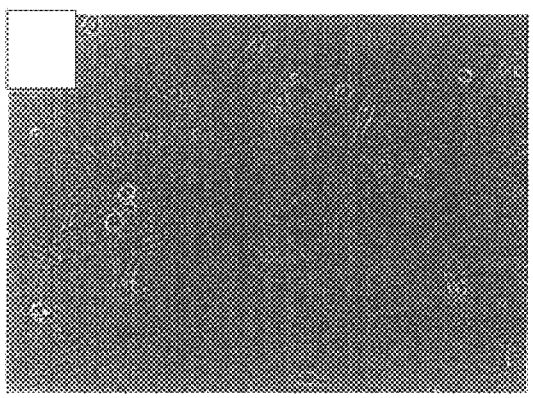
Figure 1D:

As opposed to the teaching of U.S. Pat. No. 5,629,298, the primary action of adenosine in the failing heart is not to increase contractile performance, but rather to inhibit the production of myocardial TNF-α. Since TNF-α is a potent negative inotrope, the improvement in cardiac contractility with adenosine comes about through inhibiting TNF-α expression.

Every agent that has been evaluated for the treatment of congestive heart failure that acts by augmenting intracellular cyclic AMP levels has been associated with a substantial increase in mortality. Thus, if adenosine functioned as proposed by of U.S. Pat. No. 5,629,298, it would be expected that long term use would be associated with increased mortality.

Because TNF-α is responsible for remodeling of the failing myocardium, including fibrosis, interstitial infiltrates, cellular hypertrophy, abnormal calcium homeostasis, remodeling of the interstitial matrix, uncoupling of the adrenergic receptor from adenylyl cyclase, and abnormalities in the function of tyrosine kinase receptor mediated pathways, the use of a cytokine antagonist such as adenosine (or other agents that increase intracellular adenosine) are expected to prevent maladaptive remodeling in injured or failing myocardium and in so doing improve survival and decrease hospitalizations. Another way of describing this phenomenon is that an anti-cytokine strategy can delay the transition from compensated to decompensated CHF. The best example of an agent that appears to work through a similar mechanism is an angiotensin converting enzyme inhibitor.

U.S. Pat. No. 5,629,298 proposes that adenosine itself is not beneficial in treating abnormal contractile performance of the heart. This is not true. The $A_1$ adenosine receptor mediates vasodilation. However, peripheral vasoconstriction and increased afterload is a major component of congestive failure. Indeed, many pharmacologic agents including low dose dopamine, hydrazine, nitrates, angiotensin converting enzyme inhibitors and nitroprusside have been used successfully in the treatment of patients with congestive heart failure because of their vasodilating properties. Since peripheral vascular resistance is elevated in virtually all patients with congestive failure, the vasodilating properties of adenosine coupled with the anticytokine properties would be of great benefit in these patients for acute failure. Additionally, the combination of dobutamine, a potent adrenergic agonist, in combination with adenosine would be expected to have marked synergistic effects.

In Dobson, it was noted that the normal intact myocardium did not show an increase in contractility when exposed to adenosine. However, both ischemic rat myocardium and isolated adult myocytes in culture showed enhanced contractility when exposed to adenosine. Dobson does not explain this disparity. Nor does he point out that every "inotropic agent" by definition should improve contractility in both normal and failing myocardium. Therefore, adenosine cannot be considered an "inotropic agent." The reason for this disparity in the Dobson application is illustrated in the present application. We clearly demonstrate that normal myocardium does not express TNF-α. However, failing heart robustly reexpress TNF-α. Therefore, adenosine decreases TNF-α levels in the failing heart but can have no effect on TNF-α levels in the normal heart since no TNF-α is being produced. In contrast to samples of whole heart, adult myocytes in culture produce substantial quantities of TNF-α. This TNF-α diminishes cardiac contractility by virtue of its being a potent "negative inotrope" (this negative inotropic property can be seen in all types of heart muscle preparations). Therefore, when adenosine or adenosine $A_2$ agonists are used to treat adult myocytes in culture, there is a decrease in TNF-α expression with a concomitant improvement in myocyte contractility. Hence, adenosine and $A_2$ agonists are not "inotropes" but rather are "anti-cytokine" agents.

It has also been suggested that adenosine $A_2$ agonists are inotropes. However, adenosine and $A_2$ agonists improve the diastolic properties of the heart and also normalize calcium homeostasis, and are equally important lusitropic actions. This again differentiates them from "inotropics" which by definition have only inotropic properties (although a few inotropes have modest lusitropic properties as well because of ancillary effects). An agent with both inotropic and lusitropic properties has a much wider array of uses than one with pure inotropic properties. The reason why most inotropic agents do not have lusitropic effects is that the down-regulation of expression of phospholamban and calcium ATPase inhibits the ability of the sarcoplasmic reticulum to take up calcium. It is this process that is critical for normal cardiac relaxation. Simply increasing intracellular cyclic AMP has only a trivial effect on parameters of relaxation and has not been shown in experimental studies to improve relaxation or calcium homeostasis. However, the down-regulation of phospholamban and calcium ATPase expression is down-regulated by the proinflammatory cytokines during heart failure. Therefore, antagonism of TNF-α expression by adenosine or adenosine $A_2$ agonists results in improved calcium homeostasis by allowing for the up-regulation of these critically important cardiac proteins. Furthermore, it points to the fact that the major benefits of adenosine do not come from increasing contractile performance.

An agent that increases contractile performance is not used in patients with compensated cardiac function. For example, none of the intravenous inotropic agents are approved for use in patients with congestive heart failure who are either asymptomatic or have mild symptoms (New York Heart Association Class 1, II, or early III). The results of the numerous Digoxin studies also suggest that this agent should not be utilized in patients with minimal symptoms. However, because of the role of TNF-α and proinflammatory cytokines in initiating maladaptive remodeling (including fibrosis, abnormal calcium homeostasis, interstitial infiltrates, receptor uncoupling, cardiac dilation, etc.), we expect that an anti-cytokine agent would be of benefit and indeed might be of greatest benefit in the earlier stages of congestive heart failure. Many patients with early congestive heart failure and minimal symptoms do not express the proinflammatory cytokines. Therefore, an anti-cytokine agent would prevent or at least delay the eventual expression of cytokines and by doing so preserve more normal cardiac morphology and prolong survival and the onset of worsening CHF. Similarly, an anti-cytokine agent—in marked contrast with an inotropic agent—would be beneficial in patients after a myocardial infarction where damage has occurred but maladaptive remodeling has not yet started. To date, inotropic agents (including digoxin) are contraindicated in patients with a recent myocardial infarction, myocardial damage and a decreased ejection fraction, but no symptoms of heart failure as well as in those with minimal symptoms that respond rapidly to diuretics and an angiotensin converting enzyme inhibitor. However, we propose that adenosine or adenosine $A_2$ agonists (or agents that increase myocardial adenosine production) would be of great benefit in these patients because it would blunt eventual cytokine expression and the development of maladaptive remodeling.

Adenosine has been given in a large number of clinical situations with little or no side effects. Furthermore, in the patient with CHF, there is increased peripheral vascular resistance, which is lessened with adenosine resulting in increased cardiac output. Therefore, the dangers of such pharmacologic therapy in this patient population is trivial. U.S. Pat. No. 5,629,298 suggests using echocardiography and electrocardiography in these patients. It is unlikely that this is necessary as long as the patient does not have an A-V conduction delay prior to therapy. In acutely ill patients, a Swann Ganz catheter is usually used for patient monitoring when any medications are given. However, in Class I or Class II NYHA patient an adenosine analog can be given without special precautions (outside of the context of initial clinical trials and evaluations). Most importantly, recent studies show that the intracoronary administration of adenosine has no effect on myocardial function or AV conduction.

II. Increasing Cellular Availability Of Adenosine Inhibiting Cardiac Expression of TNF-α

1. TNF-α is a key mediator of cellular damage.

Tumor necrosis factor alpha (TNF-α) is a key mediator of cellular damage in immune and inflammatory responses. Only recently has TNF-α been found to play a role, in the myocardium. In 1990, it was first noted that patients with congestive heart failure have elevated levels of TNF-α Subsequently, investigators demonstrated that failing, but not normal human myocardium, expresses TNF-α. Additionally, there is an inverse relationship between TNF-α levels and New York Heart Association classification of disease severity. That elevated levels of TNF-α are not simply an epiphenomenon is demonstrated by the observation that when TNF-α is robustly overexpressed in the myocardium of transgenic animals, the mice develop a lethal Cardiomyopathy. In contrast, a more modest level of overexpression results in the development of a dilated Cardiomyopathy in transgenic animals. Similarly, continuous infusion of TNF-α results in the development of a dilated Cardiomyopathy in rodents. Furthermore, TNF-α re-expression effects a re-expression of myocardial 1L-1B. Although myocyte TNF-α expression is elevated with failure, little is known regarding the molecular and cellular mechanisms that regulate myocardial TNF-α expression.

Recently, investigators have demonstrated that the ability of macrophages to express TNF-α could be attenuated by adenosine. Furthermore, a recent study suggests that patients harboring a single mutant allele of the AMP deminase gene, a mutation with the potential to increase myocardial adenosine production, have a marked delay in the onset of symptoms of end-stage congestive heart failure. Additionally, adenosine has been shown in numerous studies to have a cardioprotective effect in myocardial ischemia. Therefore, we hypothesized that adenosine might regulate expression of cardiac TNF-α. We present herein data suggesting that physiologic concentrations of adenosine can attenuate expression of TNF-α by lipopolysaccharide (LPS) stimulated neonatal rat cardiomyocytes, adult rat ventricular myocytes and rat pillory muscle.

2. Neonatal rat cardiomyocytes.

Isolation. Cardiomyocytes were prepared from ventricles of one day old Sprague-Dawley rats by the method of Toraason et al. as previously described using a commercially available cardiomyocyte isolation kit (Worthington Biochemical. Freehold, N.J.). Cells recovered after trypsin and collaenode digestion were preplated on untreated plastic flasks for 1 hour to reduce non-myocyte cell numbers. Non-adherent cells enriched for cardiomyocytes were cultured in DMEM/F12 containing 5% horse serum. I mmol/L glutamine. 10 mmol/L HEPES, 0.1 mmol/L bromodeoxyuridine, 5 µg/ml insulin, 5 ng/ml selenium, 5 µg/ml transferring, and 10 µg/ml gentamycin. Horse serum was treated with AGIX-10 (Pharmacia. Piscatawa, N.J.) resin as previously described to reduce serum triiodothyronine to undetectable levels as determined by rarioimmunoassay. Cells were plated on pronectin (Promega, Madison, Wis.) coated tissue culture plates at a density of 1×10 cells per cm and grown at 37° C. in 95% 5%O CO Cells were cultured for 48 hours before starting experiments.

Immunohistochemistry. To prove that neonatal myocytes express TNF-α, cells were stained with antibody to rat TNF-α (R&D systems, Minneapolis, Minn.). To determine the extend of contamination with non-myocytes, cells were stained with antibody to myosin heavy chain as previously described. Briefly, cell cultures were prepared as described above and cells grown on glass slides. Cells were washed twice in ice-cold PBS and fixed with a 1:1 mixture of methanol and acetone for 15 min at 4° C. After fixation, cells were incubated for 60 min. in 1:10 diluted goat or rabbit serum (Sigma) to limit background staining. The TNF-α antibody was used in a 1:1000 dilution, the monoclonal Antimyosin antibody (MF-20), in a 1:2 dilution. Slides were washed 3 times with ice-cold PBS and incubated for 30 min. with secondary fluorescein (FITC Sigma) labeled goat anti-mouse antibody (1:100 dilution). Slides were viewed with an inverted phase immunofluorescence microscope (Nikon). Antimyosin labeling showed that routine cell preparations contained -93% cardiomyocytes. The remaining cells consisted mainly of fibroblasts(-7%) with traces of endothelial cells and smooth muscle cells.

Fibroblasts. To determine whether contamination with fibroblasts might have influenced our results, experiments with fibroblast rich preparations were performed. Fibroblast rich preparations were obtained at the time of pre-plating. Cells were grown to confluence in DMEM/F12 containing 5% horse serum. 1 mmol/1 glutamine, 10 mmol/HEPES, 5 µb/ml insulin, 5 ng/ml selenium, 5 µg/ml transferring, and 10 µg/ml gentamycin. Less than 5% cardiomyocyetes were present in fibroblast rich preparations.

Chemiluminescense. Control studies were performed to determine whether contamination of the cardiomyocyte cultures with leukocytes (macrophages, monocytes, and neutrophils) may have contributed to TNF-α production. We used Chemiluminescense to assess the extent of contamination with leukocytes as previously described. The principle behind chemiluminescence is that it occurs naturally during phagocytosis, can be potentiated with a chemiluminescent. and correlates with the number of leukocytes. In brief, cardiomyocyte cultures were prepared as described above and 10 µg/ml phorbol myristate acetate (PMA) or 100 ng/ml LPS E. coli 0127) were added to induce phagocytosis. Chermiluminescense signal was measured in a luminometer (Lumat, Berthold Systems Inc, Pittsburgh, Pa.) using 10 µmol/L luminol (Sigma) as chemiluminescrent. Minimal chemiluminescence was induced by adding PMA or LPS to the cardiomyocyte cultures. We estimated that the number of contaminating leukocytes was<250 per ml or 0.1% of the cell population.

3. Adult rat ventricular myocytes.

Isolation. Adult rat ventricular myocytes were isolated from female rates (-250 g) as previously described. Briefly, hearts were perfused by the Langendorff method with HEPES-buffered Krebs-Heinseleit solution (pH 7.4, 37° C.) containing (in mmol/L): NaCl 118, KCl 5, $KH_2PO_4$ 1, $MgSO_4$ 1, HEPES 25, $NaHCO_3$ 37.5, Glucose 11, Pyruvate 5, bovine serum alburnine 0.5% and vitamins. Myocyes were isolated by addition of collagenase (0.8 mg/ml) (Worthington). The preparations were enriched with viable myocytes by sequential sedimentations through 5% bovine serum albumin (Sigma). Cells were transferred to serum free M199 medium (Sigma) containing 5 $\mu$g/ml insulin, 5 $\mu$g/ml transferrin and 10 $\mu$g/ml gentamycin and attached to bovine serum coated 60 mm dishes. The medium was changed after 1 hour. Cells were kept at 37° C. in 95%/5% $O_2/CO_2$ for 24 hours. This procedure typically resulted in preparations containing -95% rod-shaped cardiomyocytes after 24 hours in culture. The limulus amebocyte lysate assay (E-Toxate, Sigma) was used to assess endotoxin presence during cell isolation.

4. Rat papillary muscle.

Rat papillary muscles were isolated from female rates (-250 g) and immediately cut into -2×1×1 mm strips. The muscle strips were incubated in DMEM/F12 medium containing 5% horse serum, 1 mMOL/L glutamine, 10 mmol/L HEPES, 5 $\mu$g/ml insulin. 5 ng/ml selenium, 5 $\mu$g/ml transferring, and 10 $\mu$g/ml gentamycin. Muscle strips were equilibrated for I hour at 37° C. in 95%/5% $O_2/CO_2$ before starting experiments. During the experiment muscle strips were kept in commercially available 12-well plates at 37° C. in 95%/5% $O_2/CO_2$. The weight of muscle strips was determined at the end of the experiments.

5. Stimulation with LPS.

Exposure to LPS was used to induce production of TNF-$\alpha$ in neonatal rat cardiomyocytes, in adult rat ventricular myocytes and in rat papillary muscle preparations. We used LPS of *E. coli* 0127 (Sigma, St. Louis, Mo.) after preliminary experiments had shown a rank order of TNF-$\alpha$ response: LPS *E. coli* 0127>*E. Coli* 055: B5>*Salmonella enteritis*>*Salmonella typhimurin.*

Neonatal rat cardiomyocytes were exposed to LPS (10 ng/ml/ 6 hour incubation) after 48 hours in culture. A higher dose of LPS (10 $\mu$g/ml) was necessary to induce TNF-$\alpha$ production in adult rat ventricular myocytes and rat papillary muscle. Adult rat ventricular myocytes were exposed to LPS (10 $\mu$g/ml. 6 hour incubation) after 24 hours in culture. Rat papillary muscle strips were exposed to LPS (10 $\mu$g/ml. 6 hour incubation) after a one hour equilibration period. Adenosine, adenosine receptor agonists and antagonists, and all other inhibitors were added with LPS unless stated otherwise.

6. Measurement of TNF-$\alpha$

Measurement of TNF-$\alpha$. Release of TNF-$\alpha$ into the medium was determined in neonatal and adult cardiomyocytes and in preparations of papillary muscle strips. At time 0, 3 and 6 hours after addition of LPS *E. coli* 0127, the supernatants were collected, immediately frozen in liquid nitrogen and stored at $-70°$ C. until analysis. The levels of TNF-$\alpha$ in the supernatants were measured with a rat TNF-(x enzyme linked immunosorbent assay (ELISA) kit (Factor-'test-X™, Genzme, Cambridge, Mass.). This kit uses the multiple antibody sandwich principle. The accuracy of this ELISA kit was verified by repeating measurements with a mouse TNF-$\alpha$ ELISA kit which has the property to cross-react with rat TNF-$\alpha$ (Genzyme). Both kits provided comparable measurements of TNF-$\alpha$ in our rat cardiomyocyte cell cultures. The rat TNF-$\alpha$ ELISA kit has a lower limit of detection of 10 pg/ml. In order to detect levels as low as 1 pg/ml. all samples were concentrated through centricon 10 concentrators (Amicon, Beverly, Mass.) as previously described. Recovery was equal for all measured samples and the filtrate did not contain measurable TNF-$\alpha$. For soluble TNF-$\alpha$, data are reported as pg/ml of unconcentrated supermatant.

Intracellular TNF-$\alpha$. Intracellular TNF-$\alpha$ was determined in preparations of neonatal and adult cardiomyocytes. Cells were suspended in ice-cold PBS (200 $\mu$l) with protease inhibitor phenylmethylsolfonyl fluoride (1 mmol/L) and homogenized as previously described. Cell homogenates were briefly centrifuiged to remove excess particulate matter. Total protein levels were quantitated using a commercially available assay (Bio-Rad, Richmond, Calif.) with bovine serum albumin as a standard (0 to 2 mg/ml); TNF-$\alpha$ was expressed as ing per mg protein.

7. Analysis of cytosolic calcium and contraction-relaxation in neonatal cardiomyocytes.

Free cytosolic calcium and contractile parameters were measured in neonatal rat cardiomyocytes as previously described. Neonatal cardiomyocytes were prepared as described above, plated onto glass coverslips, and cultured in the presence of PS (*E. Coli* 0127, 100 ng/ml), LPS and adenosine (10 $\mu$mol/L) or diluent for 4 days. Preliminary analysis had shown that calcium and contraction in neonatal myocytes were not affected by short-term exposure to LPS.

Cytosolic calcium. Myocytes were loaded with the acetoxymethyl ester form of fura-2 (Molecular Probes, Eugene, Oreg.) by incubating the coverslips for 20 minutes in 2 ml of Tyrode's solution containing (in mmol/L); NaCl 137, KCl 5, Glucose 15, $MgSO_4$ 1.3. $Nah_2PO_4$, HEPES 20, $CaCl_2$ 1, as well as fara-2-AM (3 $\mu$mol/L) and D-Pluronic (Molecular Probes) (3 $\mu$l of 25% wt/wt in dimethyl sulfoxice). Myocytes were then rinsed with Tyrode's solution and maintained for 15 minutes at room temperature to allow for deesterification of the dye. Coverslips were transferred to a temperature regulated chamber (33° C.) mounted on a Nikon Diaphot 300 inverted microscope stage and cells perfused with prewarmed modified Tyrode's solution. Cells were paced by electrical field stimulation at 1 Hz (15 V. 4 ms pulse duration) (Grass S11 Stimulator. Grass Instruments) using platinum electrodes. Fluorescence of intracellular fura-2 was determined by alternatively illuminating cells with 340- and 280-nm light and measuring emission at 520 nm (Ionoptix Corporation, Milton, Mass.). The sampling rate for collection of ratio values was 100 Hz. Theoretically, free cytosolic calcium ion concentrations can be calculated from the fura-2 fluorescence ratios at two wavelengths. However, improper calibration of fura-2 is difficult to exclude because of compartmentalization in loaded cells and differences in spectral properties between cells and buffer solutions. The fiura-2 fluorescence ratio was used as an indicator of free cellular calcium as previously reported.

Contraction and relaxation parameters. To provide high contrast spots for tracking contractile activity, glass beads (2.1±0.5 $\mu$m.g, Duke Scientific Corp.) were added to the neonatal myocytes. The preparation was illuminated with red light through a dichroic mirror and a video edge-detection system (VED 104, Crescent Electronics) was used to record the motion of glass beads attached to the surface of contracting myocytes. Data from 10 consecutive beats from 8–10 cells were recorded from each coverslip; at least 4 coverslips were prepared for each condition.

Data anyalasis. A data analysis program (IonWizard 4.3. Inoptix Corp.) was used to measure fura-2 parameters (baseline and peak systolic calcium) and calculate maximum speed of contraction, maximum speed of relaxation, and peak amplitude of contraction. Calibration of contractile distance was determined by using Cell-VU grid coverslips (Erie Scientific Corp).

8. Immunohistochemistry of rat papillary muscle sections.

Immunohistochemical staining of rat papillary muscles was performed as previously described. Tissue was surrounded with OCT medium and snap frozen. Blocks were cut on a cryostat at 10 microns and sections mounted on Superfrost Plus slides (Fisher, Pittsburgh, Pa.). Tissue sections were immersion fixed in 95% ethanol, rinsed in PBS and treated for 30 minutes with 5% goat serum. Sections were treated with rabbit anti-human TNF-α (Genzyme) in a 1:100 dilution for 24 hours at 4° C. This antibody binds human TNF-α- and rat TNF-α. Sections were rinsed briefly with PBS and then treated with a 1:200 dilution of biotinylated goat anti-rabbit secondary antibody (Caltag, San Francisco, Calif.). After rinsing with PBS, sections were treated with avidin-biotin complex (Vector Laboratories, Burlingame, Calif.) for one hours. Visualization of the reaction was achieved by adding 0.01% 3.3'-diaminobenzidine (DAB), 0.6% nickel ammonium sulfate, 0.05% imidazole, and 0.0003% $H_2O_2$ in 0.05 mmol/L Tris buffer. Sections were weakly counterstained with 1% Neutral Red.

Adenosine, 2-chloroadenosine. 5'-(N-ethylcarboxamide)-adenosine (NECA) and N'-cyclopentyladenosine (CPa.) were obtained from Signma. Dipyridamole, PD-125944 (DPMA), N-benzyl-5'-N-ethyl carboxamideadenosine (N-Benzyl-NECA). 3.7-Dimethyl-1-propargl xanthine (DMPX). Ro 20-1724, forskolin, 8-Bromo-cAMP sodium. MDL-12.330 and iodotubercidin (Itu) were obtained from Research Biochemcicals International (RBI. Natick, Mass.). the Antimyosin antibody MF-20 was obtained from the Developmental Studies Hybridoma Bank maintained by the Department of Pharmacology and Molecular Science, Johns Hopkins University School of Medicine, Baltimore, Md., and the Department of Biological Sciences, University of Iowa, Iowa City, Iowa, under contract NO1-HD-2-3144 from the NICHd.

9. Statistical analysis.

Results are expressed as means±SEM of duplicate determinations of at least three different experiments. Data were subjected to analysis of variance (one-way ANOVA, Fisher test), and a value of $p<0.05$ was considered to be statistically significant.

10. Immunostaining of neonatal cariomyocytes.

The extent of contamination of neonatal myocyte preparations with non-myocytes was determined by staining cells with antibody to myosin heavy chain. FIG. 1 A/B shows a routing preparation consisting of 93% cardiomyocytes. To demonstrates that neonatal myocytes express TNF-α, cells were stained with antibody to rat TNF-α after exposure to LPS 10 ng/ml for 6 hours; in the absence of LPS. TNF-α could not be demonstrated with this technique.

11. Release of TNF-α by neonatal cardiomyocytes.

In accordance with our inmmunostaining findings, neonatal rat cardiomyocytes did not release detectable amounts of TNF-α in the supernatant in the absence of LPS. The limit of detection for TNF-α was 1 pg/ml. However, in the present of LPS (E. coli 0127), TNF-α increased rapidly, reaching a peak at 6 hours. The maximum effect was seen at 10 ng/ml of LPS (46.0°2.1 pg/ml at 3 hours and 70.1±3.5 pg/ml at 6 hours; n=15). The lowest dose of LPS to elicit a significant release of TNF-α was 1 ng/ml (9.7±0.5 pg/ml at 3 hours and 22.2±2.3 pg/ml at 6 hours; n=3). To verify whether the presence of serum might influence the effect of LPS, some experiments were also performed in serum-free medium. The absence of serum did not significantly alter the response of neonatal myocytes to LPS. However, cell beating appeared diminished and less synchronous in serum-fee medium. Therefore, all further experiments with neonatal myocytes were perfumed in serum-rich medium.

12. Effect of adenosine of TNF-α release by neonatal cardiomyocytes.

Figure 2:
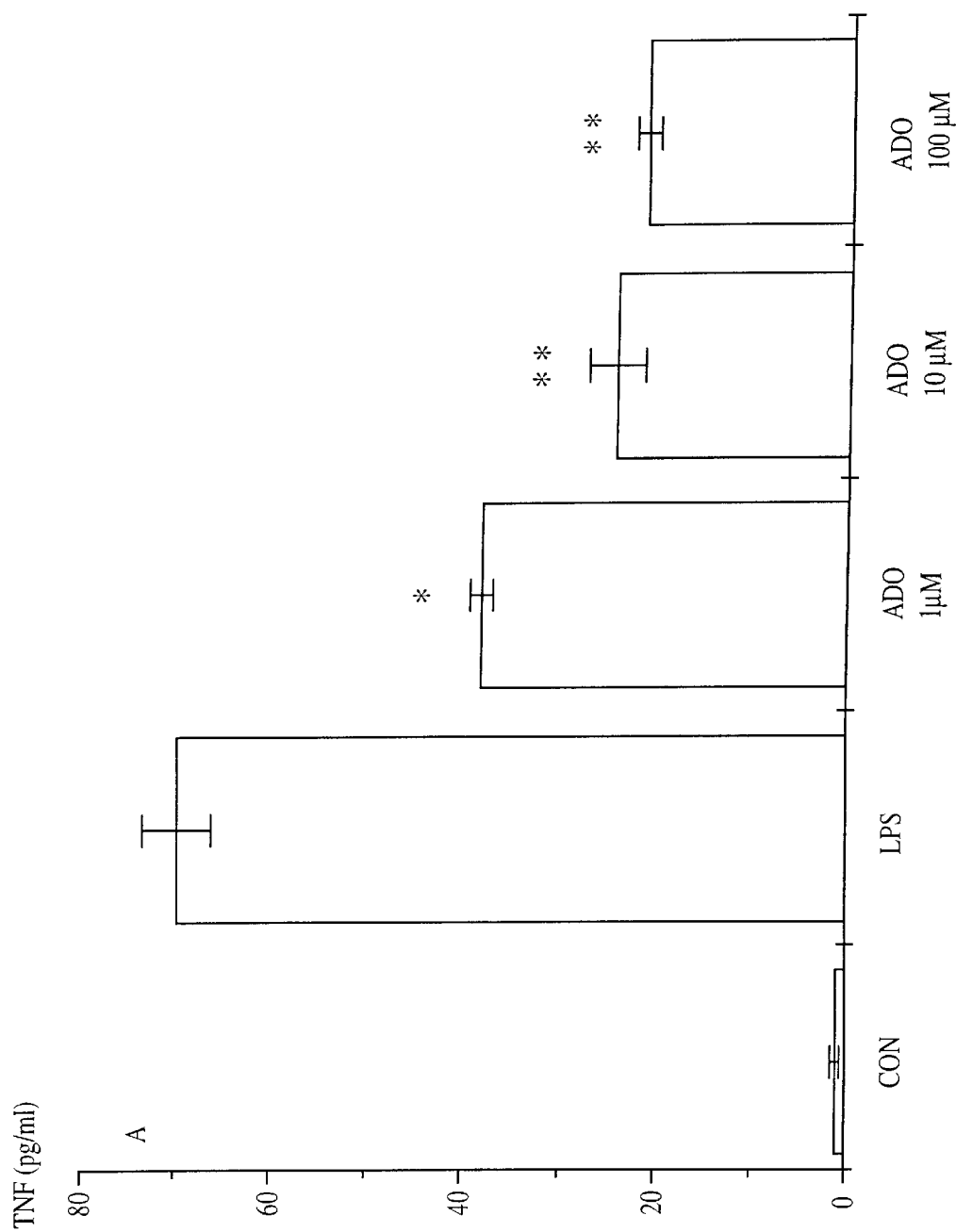
FIG. 2. Neonatal rat cardiomyocytes were stimulated with 10 ng/ml LPS (*E. coli* 0127) at time 0. After 6 hours, supernatant was collected and TNF-α was measured with ELISA. Control: in the absence of LPS, TNF-α was below the limit of detection (1 pg/ml). (A) Dose-effect of adenosine. Adenosine 1–100 μmol/L was added at time 0.
Figure 3:
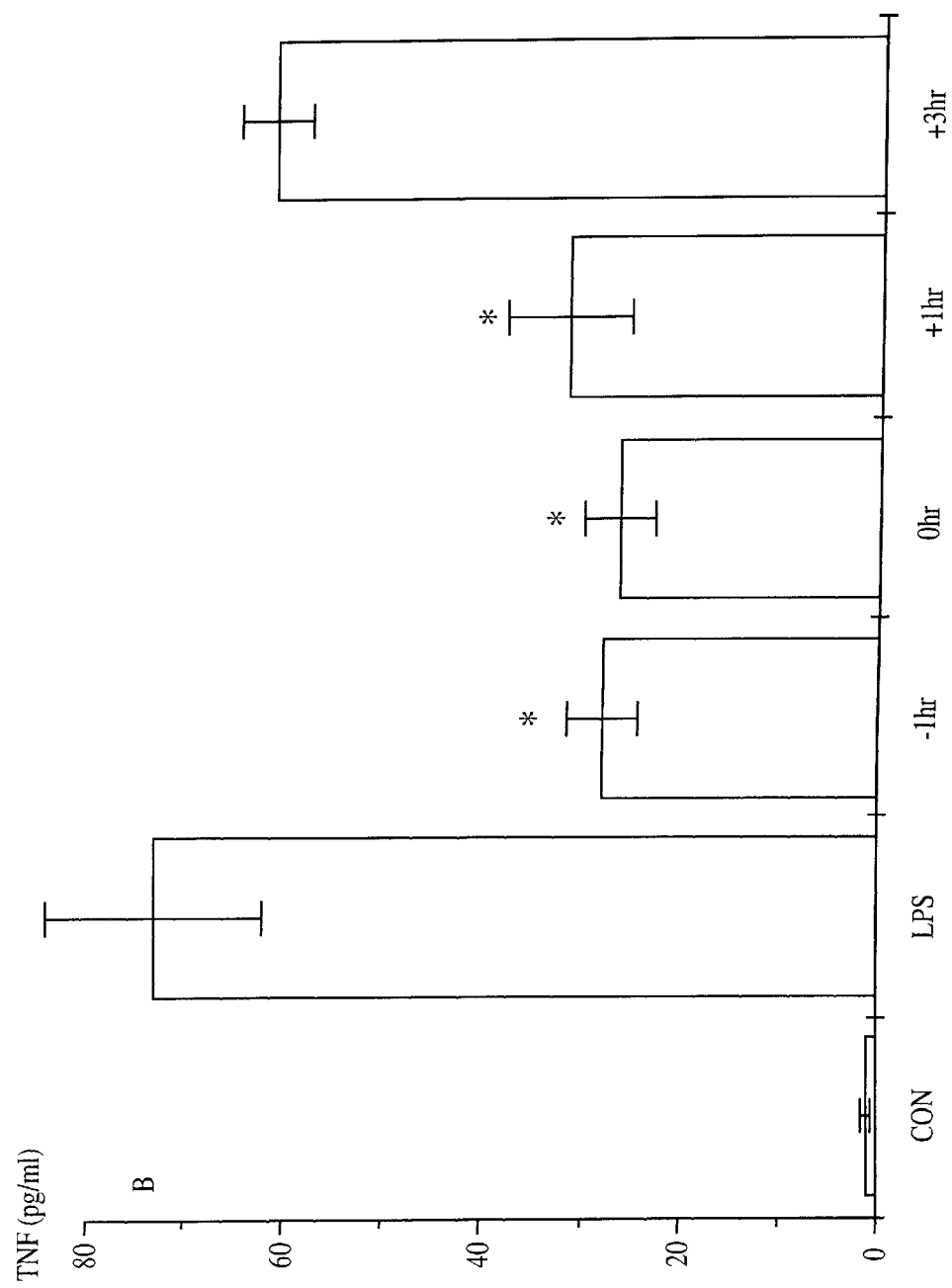
FIG. 3. (B) Timing of adenosine addition. Adenosine (10 μmol/L) was added 1 hour before LPS (-1 hr), at the same time than LPS (0 hr), 1 hour after LPS (+1 hr) and 3 hours after LPS (+3 hr). *p<0.001 and **p<0.0001 vs. LPS (n=3, ANOVA).

As seen in FIG. 2, adenosine decreased TNF-α release in a concentration-dependent manner. Adenosine was equally effective in the presence of either 100 ng/ml Y 1 ng/ml LPS (data not shown). the inhibitory effect of adenosine were not temporally related to activation by LPS as there was no significant difference between levels of inhibition when myocytes were exposed to adenosine one hour before LPS, at the time of LPS exposure, or one hour after LPS treatment (FIG. 3). However, when cells were exposed to adenosine three hours after LPS challenge, adenosine was not effective in attenuating myocyte TNF-α expression.

13. Effect of adenosine on intracellular TNF-α production.

To assess the effects of adenosine on myocyte TNF-α levels, we measured the concentration of immunogenic TNF-α. Using our measurement system we were unable to detect intracellular TNF-α at baseline. However, after addition of LPS, TNF-α levels were detectable in cell homogenates (18.2±4.3 pg TNF-α per mg of protein). In addition, 10 μmol/L adenosine decreased TNF-α to 4.0±0.4 pg per mg of protein (78% decrease, p<0.0001) (n=5).

14. Effect of adenosine regulating agents on TNF-α

Figure 4:
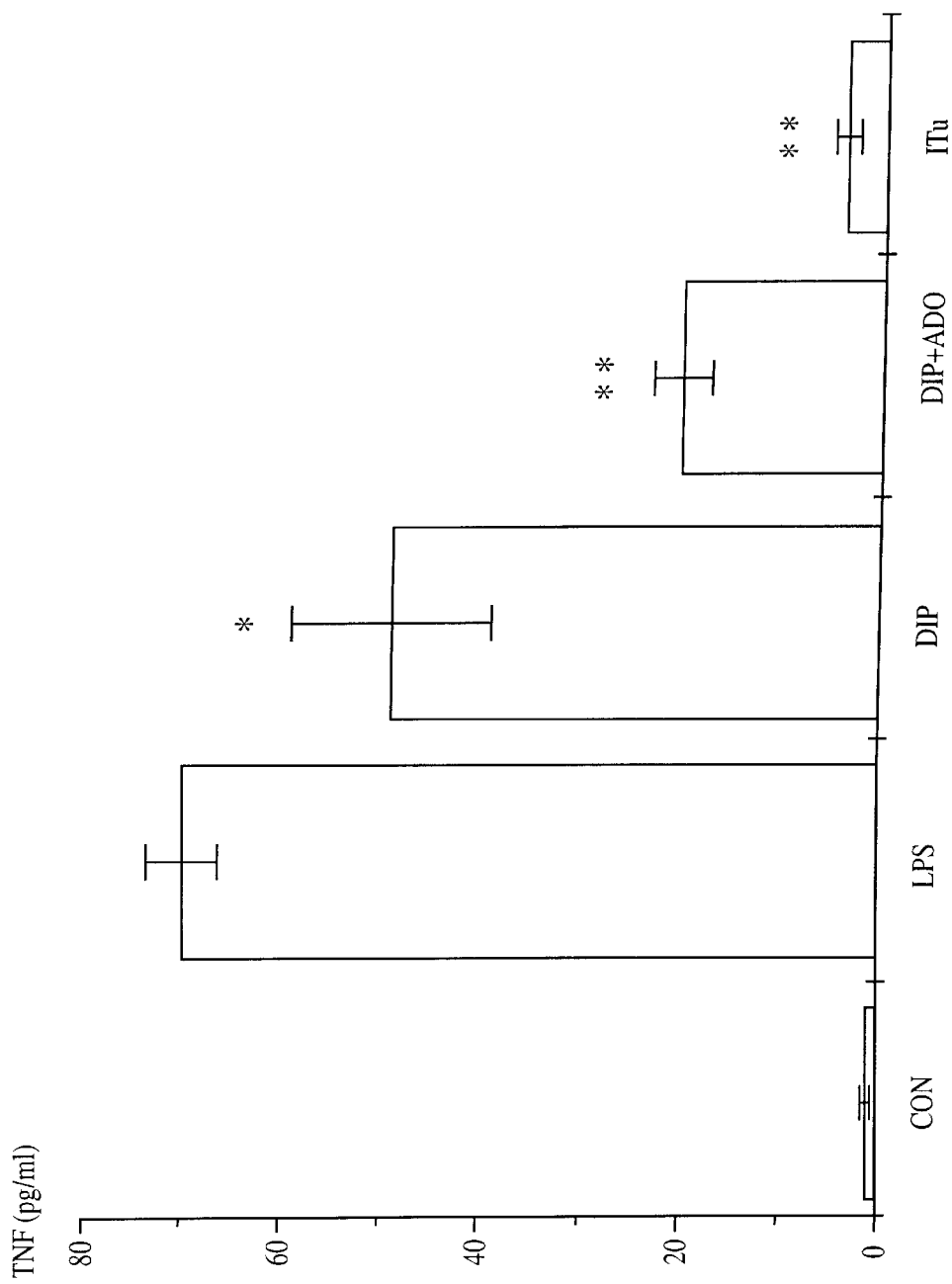
FIG. 4. Effect of adenosine regulating agents. Dipyridamole, an inhibitor of adenosine transport, and iodotubercidin, an inhibitor of adenosine kinase, are known to increase endogenous adenosine in isolated cardiomyocytes. Neonatal rat cardiomyocytes were stimulated with 10 ng/ml LPS (*E. coli* 0127) at time 0. Where indicated, adenosine (ADO) 10 μmolL, dipyridamole (DIP) μmol/L and iodotubercidin (Itu) 10 μmol/L were added at time 0. After 6 hours, supernatant was collected and TNF-α was measured with ELISA. Control: in the absence of LPS, TNF-α was below the limit of detection (1 pg/ml).*p<0.05 and **p<0.0001 vs. LPS (n=3, ANOVA).

The adenosine regulating agents dipyridamole and iodotubercidin (Itu) increase endogenous adenosine in isolated cardiomyocytes. Dipyridamole is an inhibitor of adenosine transport and Itu is an inhibitor of adenosine kinase. In the presence of 10 μmol/L dipyridamole, TNF-α was decreased by 30% at 6 hours (p<0.05) (n=3) (FIG. 4). The effect of dipyridamole was less prominent than the effect of adenosine. Adenosine had a significant additive effect in experiments where both dipyridamole and adenosine were added (p<0.01). As seen in FIG. 4, addition of 10 μmol/L Itu completely suppressed the release of TNF-α (p<0.0001). These changes were not due to cell death as myocytes maintained regular beating at the end of incubations with Itu.

15. Effect of selective adenosine agonists and antagonists.

Figure 5:
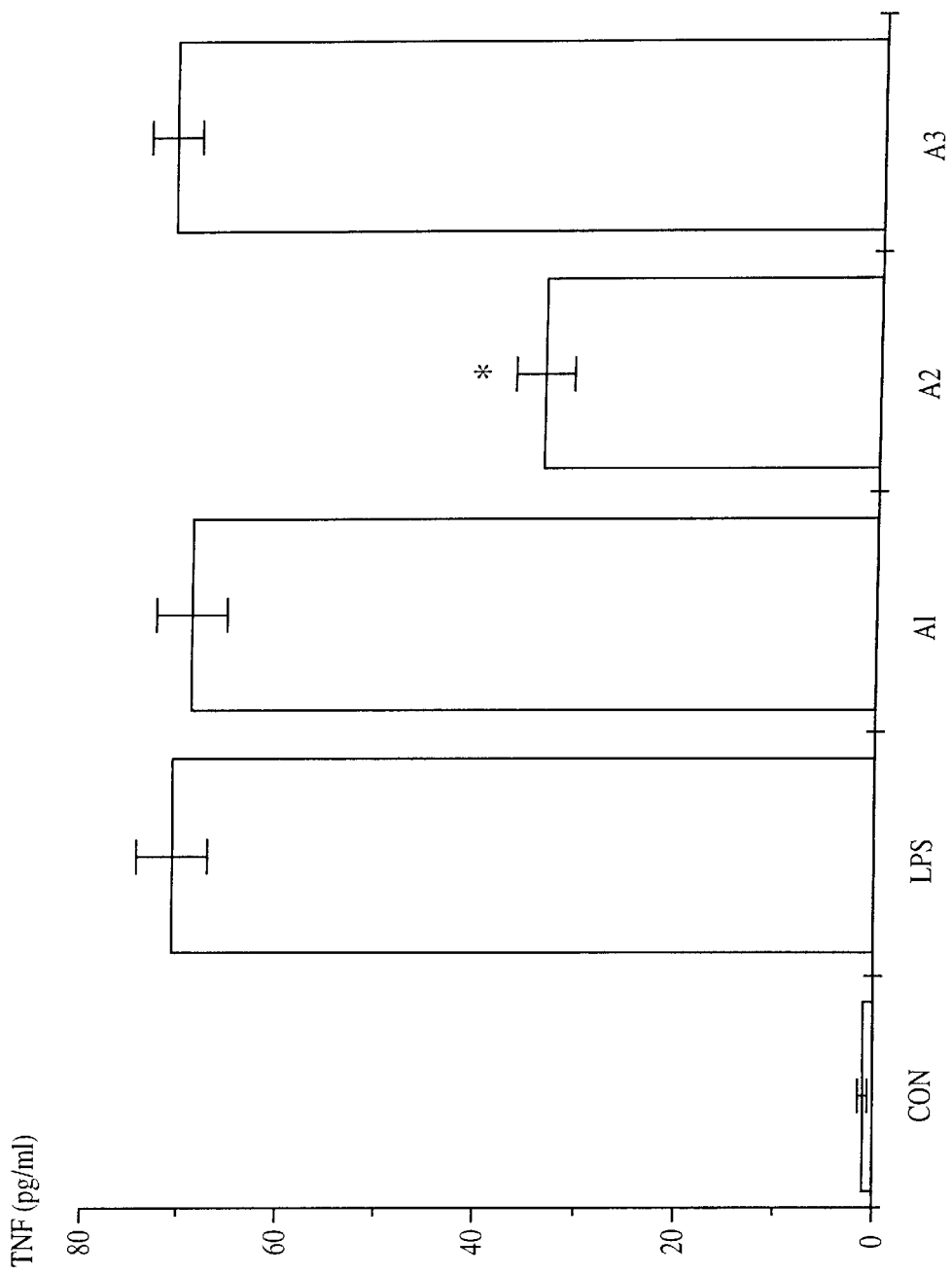
FIG. 5. Effect of adenosine receptor agonists. Neonatal rat cardiomyocytes were stimulated with 10 ng/ml LPS (*E. coli* 0127) at time 0. Selective adenosine receptor agonists CPA ($A_1$ receptor) (5 nmol/L), DPMA ($A_2$ receptor) (10 nmol/L) and B-NECA (A3 receptor) (10 nmol/L) were added at time 0. After 6 hours, supernatant was collected and TNF-α was measured with ELISA. Control: in the absence of LPS, TNF-α was below the limit of detection (1 pg/ml). *p<0.0001 vs. LPS (n=3, ANOVA).

Addition of 10 nmol/L DPMA, a selective adenosine $A_2$ receptor agonist, decreased TNF-α by 48% (p<0.001) and 52% (p<0.0001) at 3 and 6 hours, respectively (n=3) (FIG. 5). The selective adenosine $A_1$ receptor agonist CPA (5 nmol/L) and the selective adenosine $A_3$ receptor agonist Benzyl-NECA (10 nmol/L), had no effect on the release of TNF-α (FIG. 5). However, at high concentrations (100 μmol/L), these selective agonists and the non-selective agonists 2-chloroadenosine ($A_2/A_1$) and NECA ($A_2/A_1$) all decreased TNF-α by - 50% probably due to non-selective stimulation of $A_2$ receptors. At 100 μmol/L DPMA completely suppressed the release of TNF-α. Consistent with the effects of adenosine $A_2$ agonists, the selective $A_2$ receptor antagonist DMPX (10 μmol/L) abrogated the adenosine (1 μmol/L),response by 50%. This change appeared to be concentrationdependent as DMPX (10 μmol/L) attenuated the resins of 10 μmol/L adenosine by only - 30% (data not shown).

16. Effect of stimulators and inhibitors of signaling pathways on TNF-α.

Figure 6:
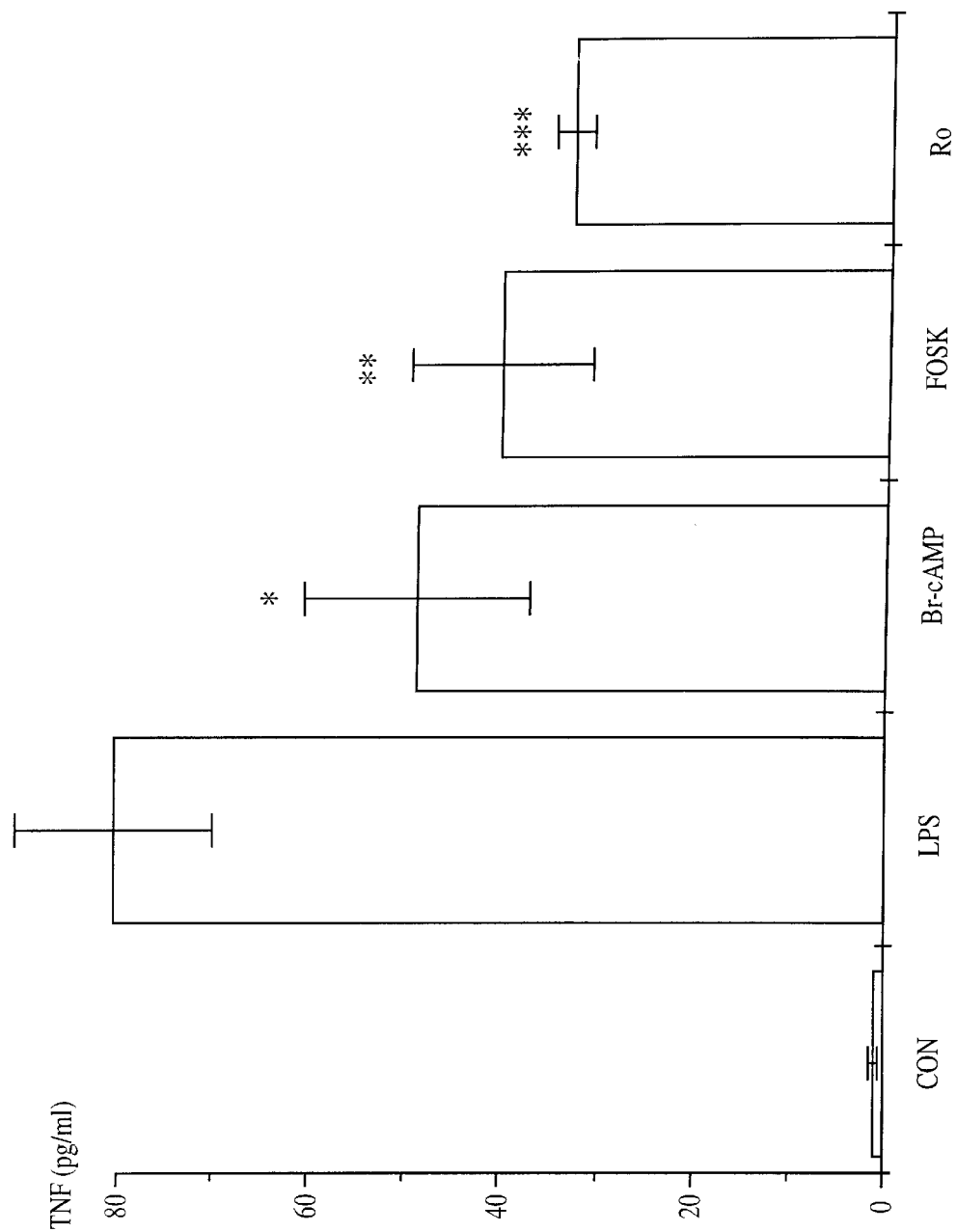
FIG. 6. Effect of cAMP agonists. Neonatal rat cardiomyocytes were stimulated with 10 ng/ml LPS (*E. coli* 0127) at time 0. Cells were treated with various agents that raise cyclic AMP: 8-Bromo-cAMP (10 μmol/L), forskolin (100 μmol/L) or Ro 20-1724(100 μmol/L) were added at time 0. After 6 hours, supernatant was collected and TNF-α was measured with ELISA. Control: in the absence of LPS, TNF-α was below the limit of detection (1 pg/ml). *p<0.005 and ***p<0.001 vs. LPS (n=3, ANOVA).

The effects of the receptor-G protein-adenylate cyclase complex (RGC) signaling pathway in mediating adenosine's inhibiton on myocardial TNF-α expression was assessed because this pathway mediates the $A_2$ response in most tissues. Utilizing pharmacologic agents known to stimulate and inhibit selective sites in the RGC pathway, we found that Ro 20-1724 (100 μmol/L), a phosphodiesterase inhibitor, decreased TNF-α by 60% (p<0.001), forskolin (100 μmol/L) by 50% (p<0.005), and 8-Bromo-cAMP (10 μmol/LO by 40% (p<0.01) (n=3) (FIG. 6). Conversely, MDL-12,330 (20 μmol/L, a specific inhibitor of adenylate cyclase, was able to completely suppress the effect of adenosine and $A_2$ agonist DPMA on TNF-α (data not shown).

17. Release of TNF-α-a by fibroblasts.

To determine whether contamination with fibroblasts (-7%) might have influenced our results, experiments with fibroblast rich preparations were performed. Fibroblast rich preparations contained -5% cardiomyocytes. FIG. 11 shows a direct comparison between cardiomyocyte and fibroblast rich preparations, each containing 100,00 cells (n=3). It can be seen that per cell, fibroblasts release -34 times less TNF-α than cardiomyocytes in response to LPS. Interestingly, neither adenosine 10 μmol/L, nor the selective $A_2$ receptor agonist DPMA 10 μmol/L had an effect of TNF-α-a release by fibroblasts. Therefore, is unlikely that contamination with fibroblasts influenced the results obtained with neonatal cardiomyocytes.

18. TNF-α production by adult ventricular myocytes.

Figure 7:
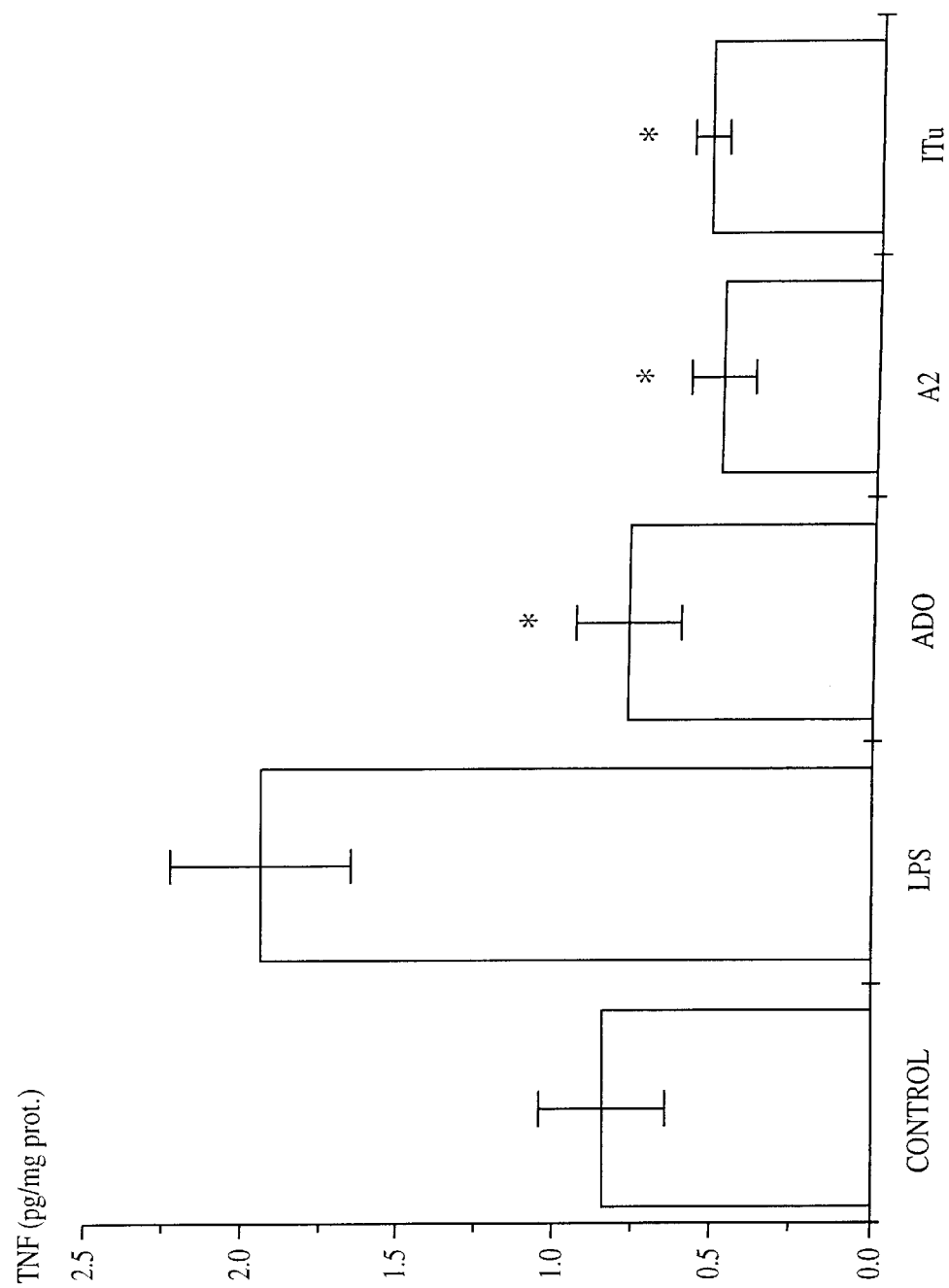
FIG. 7. Effect of adenosine on adult cardiomyocytes. Adult rat ventricular myocytes were stimulated with 10 μg/ml LPS (*E. coli* 0127) at time 0. Where indicated, adenosine (ADO) 10 g/ml LPS (*E. coli* 0127) at time 0. Where indicated, adenosine (ADO) 10 mol/L, the $A_2$ agonist DPMA 10 nmol/L or the adenosine kinase inhibitor iodotubercidin (Itu) 10 μol/L were added at time 0. After 6 hours, cell pellets were collect and intracellular TNF-α was measured with ELISA. *p<0.005 and **p<0.001 vs. LPS (n=5, ANOVA).

After, isolation through collagenase perfusion, adult ventricular myocytes stained positive for TNF-α in the absence of LPS. This was the case when myocytes were stained immediately upon isolation or after 24–96 hours in culture. As seen in FIG. 7, adult myocytes increased their production of TNF-α in response to LPS, albeit—10 times less than seen in neonatal cardiomyocytes. However, as seen in neonatal myocytes, adenosine (10 nmol/L) decreased TNF-α by 60% (p<0.005) (n=5). similarly, the $A_2$ agonist DPMA (10 μmol/L) and the adenosine regulating agent Itu (10 μmol/L) decreased TNF-α by 75% (p<0.005) and 72% (p<0.01), respectively (FIG. 7). The etiology of the baseline ativation of TNF-α after collagenase extraction in the adult myocytes may be explained by the contamination of the collagenase solution with endotoxin (>0.125 Eu/ml by limulus amebocyte lysate assay). In contrast to neonatal myocytes, we were unable to detect concentrations of TNF-α in the medium of adult caridomyocytes. However, in separate experiments we demonstrated that collagenase totally inhibits the TNF-α ELISA, thus making it likely that traces of collagenase present in the culture medium of adult myocytes were interfering with the ELISA.

19. TNF-α release by rat papillary muscle.

Figure 8A:
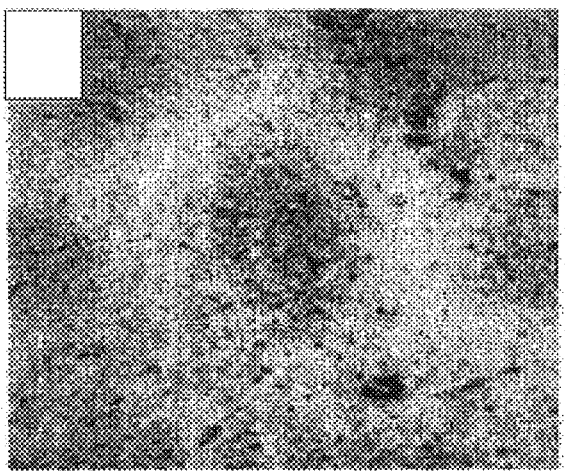
FIG. 8. Immunohistochemical analysis of TNF-α in sections of rat papillary muscles. (A) Control, (C) after treatment with LPS (*E. coli*, 10 μg/ml) for 6 hours (Magnification×200). (B) and (D) show control and LPS treatment, respectively, at higher magnification (×400). Primary antibody was stained with secondary biotinylated antibody. There is no evidence of immunostaining in the absence of LPS. LPS induces expression of TNF-α in cardiomyocytes. Sections were weakly counterstained with 1% Neutral Red.
Figure 8B:
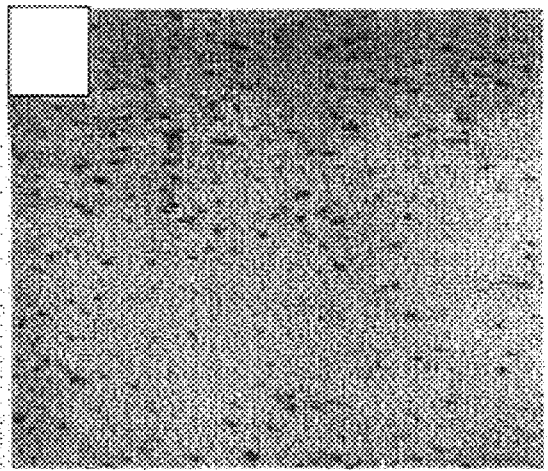
Figures 8C, 8D:
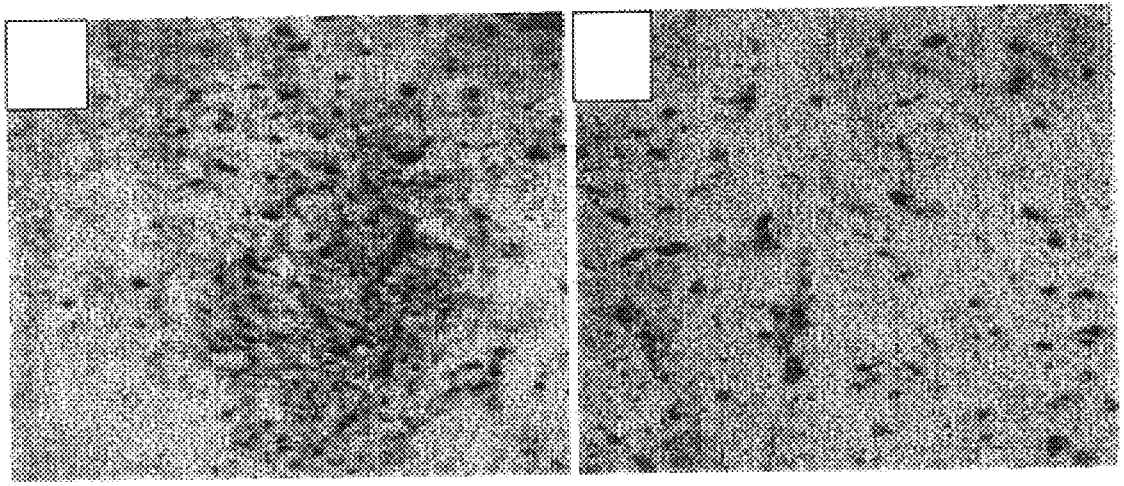
Figure 9:
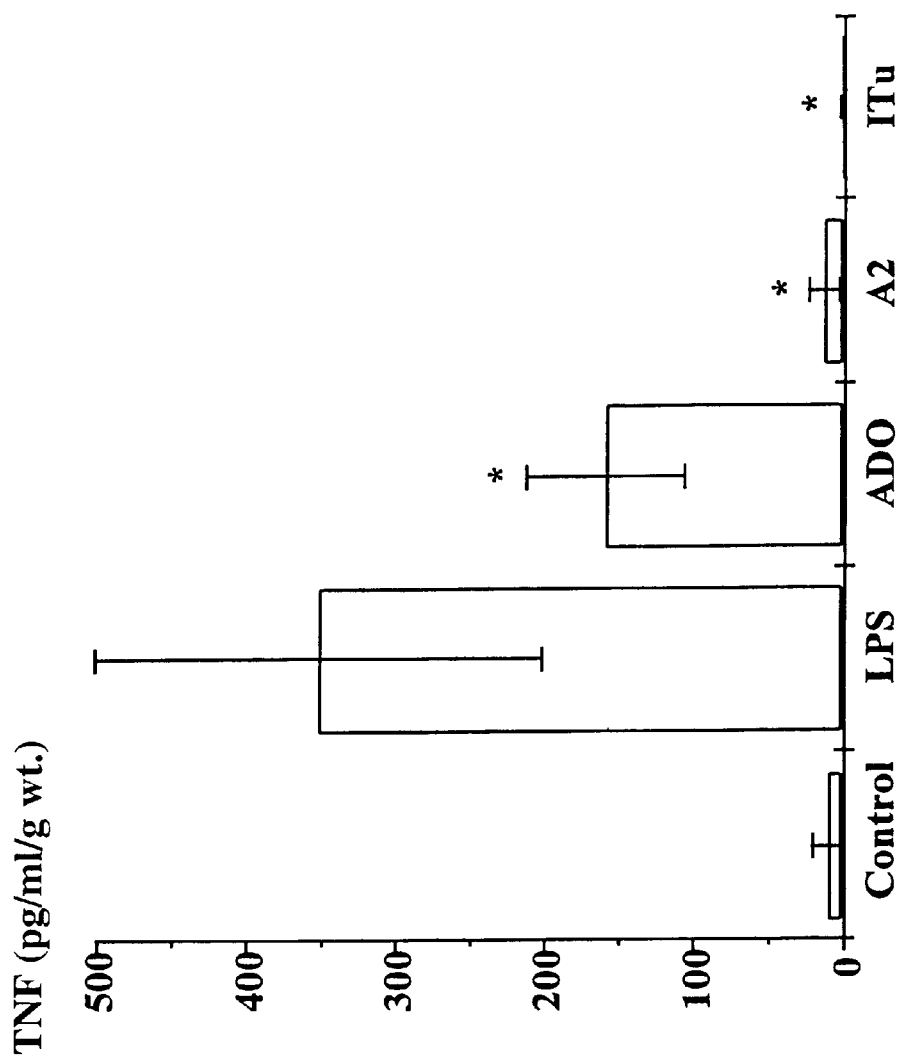
FIG. 9. Effect of adenosine on rat papillary muscles. Rat papillary muscle sections were stimulated with 10 μg/ml LPS (*E. coli* 0127) at time 0. Where indicated, adenosine (ADO) 10 μg/ml LPS (*E. coli* 0127) at time 0. Where indicated, adenosine (ADO) 10 μmol/L, the $A_2$ agonist DPMA 10 nmol/L or the adenosine kinase inhibitor iodotubercidin (Itu) 10 μgmo/L were added at time 0. After 6 hours, supernatants were collected and TNF-α was measured with ELISA. *p<0.05 and **p<0.005 vs. LPS (n=5, ANOVA).

To insure that the effects of adenosine were not limited to isolated myocytes, we also exposed rat papillary muscle sections to LPS. While normal muscle demonstrated no TNF-α, LPS initiated expression of TNF-α (FIG. 8). FIG. 8 shows that using Immunohistochemistry, myocytes were identified as a primary source of TNF-α in the papillary muscle. Adenosine 10 μmol/L also inhibited TNF-α expression in papillary muscles (FIG. 9), 55±15% reduction (p<0.05, n=5). The $A_2$ agonist DPMA 10 μmol/L and the adenosine regulating agent Itu 10 μmol/L decreased TNF-α release by papillary muscles by 96% (p<0.005) and 99% (p<0.005), respectively (FIG. 9).

20. Effect of adenosine on cytosolic calcium and contraction in neonatal myocytes.

Figure 10:
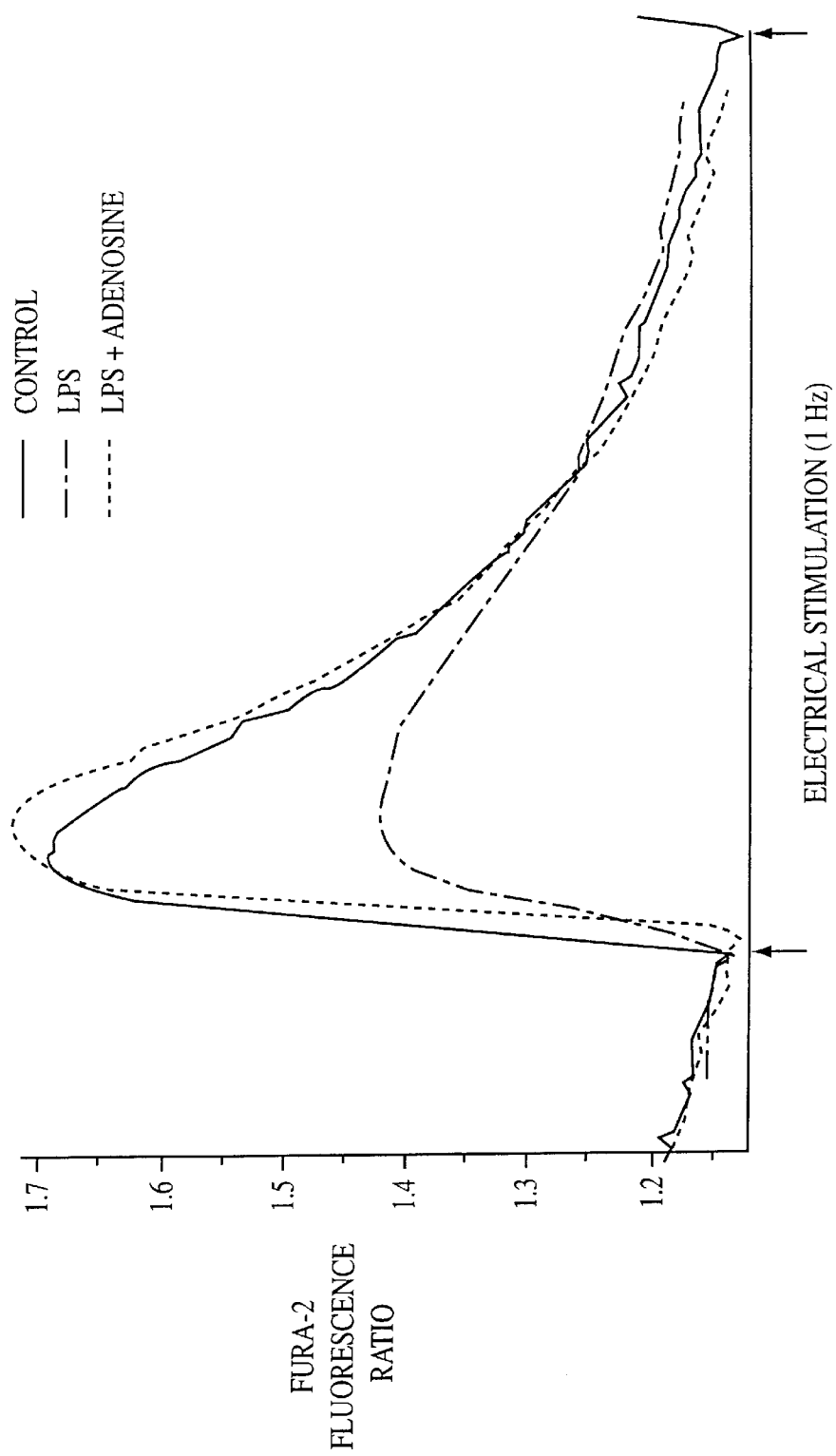
FIG. 10. Representative superimposed tracings of calcium transients in electrically driven (1 Hz) cultured rat neonatal cardiomyocytes. Myocytes were treated with diluent (control), LPS *E. coli* (100 ng/ml) and LPS plus adenosine (10 μmol/L) for 4 days; treatments were performed after isolation and repeated on days 2 and 4. Myocytes were plated on coverslips and intracellular calcium measured as fura-2 fluorescence ratio.

FIG. 10 shows a representative calcium transient of a group of normal, LPS- and adenosine-treated neonatal myocytes. Cumulative data are summarized in the table of FIG. 12. Baseline diastolic fura-2 ratio was similar in the three groups. LPS E. coli (100 ng/ml) significantly reduced the peak systolic calcium by 17% (p<0.01, n=38), this was associated with a 50% decrease (p<0.01) in shortening fraction, as well as significant decrease in contraction velocity (p<0.01) and relaxation velocity (p<0.01). As demonstrated, adenosine (10 μmol/L) totally abolished the LPS effect on sytosolic calcium. Adenosine also significantly improved shortening fraction (p<0.01), contraction velocity (p<0.01) and relaxation velocity (p<0.01). However, while contraction and relaxation parameters improved, they did not return to normal in the presence of adenosine. Measurements of TNF-α in the medium of electrically driven cells confirmed that changes in calcium and contraction due to LPS were paralleled by changes in TNF-α. Therefore, it shoudl be noted that adenosine is not "inotropic but rather improves contractility to baseline levels that would be seen without TNF-α. Additionally, these studies point out that adenosine has important effects on cardiac relaxation and therefore has lusitropic effects. This latter finding is in contrast to other agents.

The present study demonstrates that adenosine inhibits expression of TNF-α in neonatal cardiomyocytes, in adult cardiomyocytes and in rat papillary muscles. In control conditions, neonatal myocytes do not synthesize or release measurable amounts of TNF-α. However, the addition of LPS induces substantial production and release of TNF-α. This is consistent with an earlier report showing TNF-α release by neonatal mouse myocytes after admninistration of LPS. In the present study, release of TNF-α was associated with a 17% decrease in peak systolic calcium (p<0.01), a 50% decrease in contraction (p<0.01) as well as abnormal relaxation (p<0.01) in neonatal myocytes after 4 days. That TNF-α is expressed by myocytes was confirmed by immunofluorescent staining of myocytes with antimyosin and anti-TNF-α. This finding was supported by chemiluminescent analyze of WBC contamination and experiments with fibroblast-rich preparation. In contrast to neonatal myocytes, ELISA and immunostaining were able to detect TNF-α synthesis in adult myocytes in the absence of LPS. However, this was probably due to the presence of trace amounts of endotoxin in the perfusion system. Nevertheless, adult myocytes responded to LPS with enhanced TNF-α production, albeit significantly less than neonatal myocytes. These findings were consistent with earlier studies in which production of TNF-α protein occurred in feline cardiomyocytes isolated from LPS perfused hearts. In contrast to cultured adult rat myocytes, rat papillary muscles did not show evidence of baseline TNF-α stimulation by either ELISA or immunohistchemistry. However, consistent with the cultured cells, papillary muscles responded to LPS with marked TNF-α release.

In the present study we demonstrate that the addition of adenosine to the culture medium effects a significant attenuation of the release of TNF-α by neonatal cardiomyocytes. The adenosine effect was concentration-dependent and occurred with a physiologic concentration of adenosine (1 μmol/L). In addition, adenosine inhibits TNF-α release when cells were exposed to adenosine one hour before LPS treatment, at the time of LPS treatment, or up to one hour after LPS challenge. By contrast, adenosine was not effective when given three hours after LPS challenge. Furthermore, the anticytokine effects of adenosine could not be attributed to an inhibition of TNF-α release since adenosine also inhibited the cellular production of TNF-α by 78% (p<0.0001). The effect of adenosine was not limited to neonatal myocytes, as it inhibited TNF-α production in adult myocytes by 60% (p<0.005) and TNF-α release by papillary muscles by 55% (p<0.05).

The physiologic importance of our observation is illustrated by the fact that adenosine normalized LPS-induced calcium changes in neonatal myocytes (FIG. 10). This was associated with significant improvement in cardiac contraction (p<0.01) and relaxation (p<0.01). The LPS-induced calcium changes concur with known effects of TNF-α on calcium transients. However, it is unlikely that LPS induced changes were solely related to TNF-α. Indeed, it is possible that the effects of LPS on calcium and contraction were due to activation of other cytokines in the inflammatory cascade. The direct negative inotropic effects of LPS and TNF-α have been shown previously in cardiomyocytes. Our results indicate that LPS also has a significant (p<0.01) negative lusitropic effect. Adenosine significantly improved contraction and relaxation in cells exposed to LPS. That adenosine did not completely normalize contraction and relaxation may be explained by the fact that adenosine also activates the adenosine $A_1$ receptor which mediates mild negative inotropic effects in cardiomyocytes.

There are four subclasses of adenosine receptors ($A_1, A_{2a}, A_{2b}, A_3$) The cardiac $A_1$ receptor and its antiadrenergic actions are well characterized; the $A_1$ receptor appears to be coupled to activation of an inhibitory guanine nucleotide regulatory protein (Gi) and therefore decreases intracellular production of cyclic AMP. More recently, investigatores have found that $A_2$ receptors are responsible for increases in inotropy via cyclic AMe-dependent as well as cyclic AMP-independent mechanisms. However, our studies suggest that $A_2$ receptors also mediates lusitropic effects. More important are the anti-cytokine effects that cannot only be useful in acute settings but are more important in inhibiting myocardial remodeling and can then prolong survival and prevent development of worsening CHF. The presence of $A_3$ receptors on cardiomyocytes has also been proposed in recent studies. However, the physiologic role of cardiac $A_3$ receptor agonist remains undefined. These results plust the finding that DPMA inhibited TNF-α expression in the nanomolar range led us to postulate that the cytokine inhibitory effects of adenosine are mediated through an $A_2$ dependent pathway. This hypothesis was supported by the fact that the $A_2$ selective antagonist DPMX suppressed the ability of adenosine to inhibit TNF-α release. It should be noted that inhibition of TNF-α expression occurred at higher concentrations (micromolar) with the $A_1$ and $A_3$ agonists; however, this was likely due to non-selective occupancy of the $A_2$ receptor at high agonist concentration.

To further support the hypothesis that adenosine effects a robust inhibition of myocardial cytokine release, we studied the response to LPS in the presence of dipyridamole, an inhibitor of adenosine transport, and Itu, an inhibitor of adenosine kinase. Both inhibitors have been shown to increase endogenous adenosine levels in isolated cardiac myocytes. Dipyridamole decreased TNF-α by 30% with exogenous adenosine having significant additive effect. These results were consistent with results obtained by Bourna et al. in activated human monocytes exposed to draflazine, an inhibitor of adenosine transport. In contrast, the addition of Itu (10 μmol/L) totally suppressed LPS-stimulated TNF-α release. It remains unclear why Itu was more effective than exogenous adenosine. However, it is possible that in the presence of Itu, endogenous adenosine was compartmentalized with the $A_2$ receptor. The results with adenosine regulating agents were confirmed in adult cardiomyocytes and papillary muscles, where Itu (10 μM) suppressed TNF-α by 72% (p<0.01) and 99% (p<0.005), respectively. Our results obtained with adenosine regulating agents are consistent with a previous report in which draflazine, another adenosine regulating agent, attenuated TNF-α release by activated monocytes.

Previous studies have suggested that TNF-α is decreased by cyclic AMP dependent mechanisms in macrophages. The results of the present study suggest that cyclic AMP dependent mechanisms are also responsible at least in part for the inhibitory effects of adenosine on TNF-α production in myocytes. Activation of the $A_2$ receptor, a GC coupled receptor, significantly decreased TNF-α release. In addition, when intracellular cyclic AMP was increased with forskolin, 8-BromocAMP or Ro 20-1724, TNF-α was decreased by approx. 50%. Conversely, the adenylate cyclase inhibitor MDL 12,330 was able to inhibit completely the effect of adenosine and the $A_2$ agonist DPMA.

The effects of adenosine on the immune system, and in particular, its inhibitory effects on phagocyte function and adherence of neutrophils are well recognized. Recently, Parmely et al. have shown that the production of TNF-α by LPS treated macrophages can also be modulated by adenosine. They demonstrated that 1–10 μmol/L adenosine inhibited the TNF-α production of activated mouse peritoneal macrophages by at least 50%. similar results were obtained by Bourna et a. using activated human monocytes and Reinstein et al. using activated rat Kupffer cells. Therefore, the results of the present studies suggest that the inhibitory effects of adenosine on cytokine production may be a ubiquitous phenomenon. However, whether the effects of adenosine are at the pre- or posttranslational level remains to be determined. Furthermore, our results are the first to demonstrate that adenosine can effect myocardial TNF-α levels.

An increasing amount of data suggest a pathophysiologic role of cytokines in the development of the end-stage heart failure phenotype. In the present study we demonstrate that adenosine can substantially inhibit myocyte TNF-α expression in neonatal cardiomyocytes, adult cardiomyocytes and papillary muscles. If adenosine effects a similar inhibition of TNF-α expression in vivo, regulation of myocardial TNF-α expression by modulation of adenosine levels may provide a new and novel therapeutic target for the pharmacology or molecular therapy of end-stage congestive hear failure. However, adenosine only attenuated TNF-α expression when cells were exposed before or shortly after LPS activation. Therefore, the therapeutic window for anti-cytokine therapy with adenosine is large and therapy may be of most value in patients who have less robust symptoms (Class I and II). In these patients adenosine or aduosine analogs should abrogate the development of symptomatic CHF, and delay the transition from compensated to decompensated heart failure.

III. Increased Cellular Availability of Adenosine Analogs Inhibit Lipopolysaccharide-induced expression of TNF-α in the failing human heart.

1. Human trabecular muscles.

Human heart tissue was isolated from patients with end-stage Cardiomyopathy at the time of transplantation or during insertion of a left ventricular assist device (LVAD). The heart tissue was transported at 4° C. in St. Thomas cardioplegic solution and immediately cut into ~2×1×1 mm strips. the muscle strips were incubated in DMEM/1712 medium containing 5% horse serum, 1 mmol/L glutamine, 10 mmol/L HEPES, 5 μg/ml insulin, 5 ng/ml selenium, 5 μg/ml transferring, and 10 μg/ml gentamycin. Muscle strips were equilibrated for 1 hour at 37° C. in 95%/5% $O_xCO_2$ before starting experiments. During the experiment, muscle strips were kept in commercially available 12-well plates at 37° C. in 95%/5% $O_2CO_2$. The wet weight of muscle strips was determined at the end of the experiments.

Exposure to LPS *E. coli* 0127) (Sigma. St. Louis, Mo.) 10 μg/ml) was used to induce production of TNF-α in human trabecular muscle strips. At time 0 and 4 hours after addition of LPS, the supernatants were collected, immediately frozen in liquid nitrogen and stored at −70° C. until analysis. The levels of TNF-α in supernatants were measured with a human TNF-α enzyme linked immunosorbent assay (ELISA) kit (Quantikine, R&D Systems, Minneapolis, Minn.). This kit uses the multiple antibody sandwich principle. The accuracy of this ELISA kit was verified by repeating measurements with a human TNF-α ELISA from a different company (Factor-Test-X™, Cambridge, Mass.). Both kits provided comparable measurements. The human TNF-α ELISA kit has a lower limit of detection of 4.4 pg/ml. In order to detect levels as low as 1 pg/ml, all samples were concentrated through centricon 10 concentrators (Amicon, Beverly, Mass.) as previously described. Recovery was equal for all measured samples and the filtrate did not contain measurable TNF-α. Data are reported as pg/ml of unconcentrated supernatant per mg wet weight.

To study the effect of adenosine on TNF-α production, adenosine (10 μM) (Signma), the selective adenosine A, receptor agonist DPMA (10 μM) (Research Biochemicals International, RBI, Natick, Mass.) and the adenosine regulating agent iodotubercidin (10 μM) (RBI) were added to the muscle strips at time 0. Iodotubercidin (Itu) increases local adenosine concentration by inhibiting adenosine kinase. DPMA and Itu have been shown to be potent suppressers of TNF-α expression in rat myocytes and papillary muscles.

Immunohistochemical staining of trabecular muscles was performed a previously described. Tissue was surrounded with OCT medium and snap frozen. Blocks were cut on a cryostat at 10 microns and sections mounted on Superfrost Plus slides (Fisher, Pittsburgh, Pa.). Tissue sections were immersion fixed in 95% ethanol, rinsed in PBS and treated for 30 minutes with 5% goat serum. Sections were treated with rabbit anti-human TNF-α (Genzyme) in a 1:100 dilution for 24 hours at 4° C. Sections were rinsed briefly with PBS and then treated with a 1:200 dilution of biotinylated goat anti-rabbit secondary antibody (Caltag, San Francisco, Calif.). After rinsing with PBS, sections were treated with avidin-biotin complex (Vector Laboratories, Burlingame, Calif.) for one hour. Visualization of the reaction was achieved by adding 0.01% 3,3'-diaminobenzidine (DAB), 0.6% nickel ammonium sulfate, 0.05% imidazole, and 0.0003% $H_2O_2$ in 0.05 mmol/L Tris buffer. Sections were weakly counterstained with 1% Neutral Red.

Results are expressed as mean±SEM of determinations in muscle strips of - 5 mg per single condition. Data were subjected to analysis of variance (one-way ANOVA, Fisher test), and a value of $p<0.05$ was considered to be satirically significant.

FIG. 13 shows the clinical data of the seven patients. All were male, the mean age was 50±7 years (14–67). Three patients had ischemic Cardiomyopathy and four patients dilated Cardiomyopathy. All patients were in heart failure class NYHA IV at the time the tissue was obtained. All patients had a similar medical regimen at the time of operation consisting of diuretics and intravenous inotropic agents. Four patients underwent orthotopic heart transplantation. Two patients received a bientricular assist device (Thoratec) and one patient received a left ventricular assist device (Novacor). Three patients had diabetes mellitus.

Figure 14:
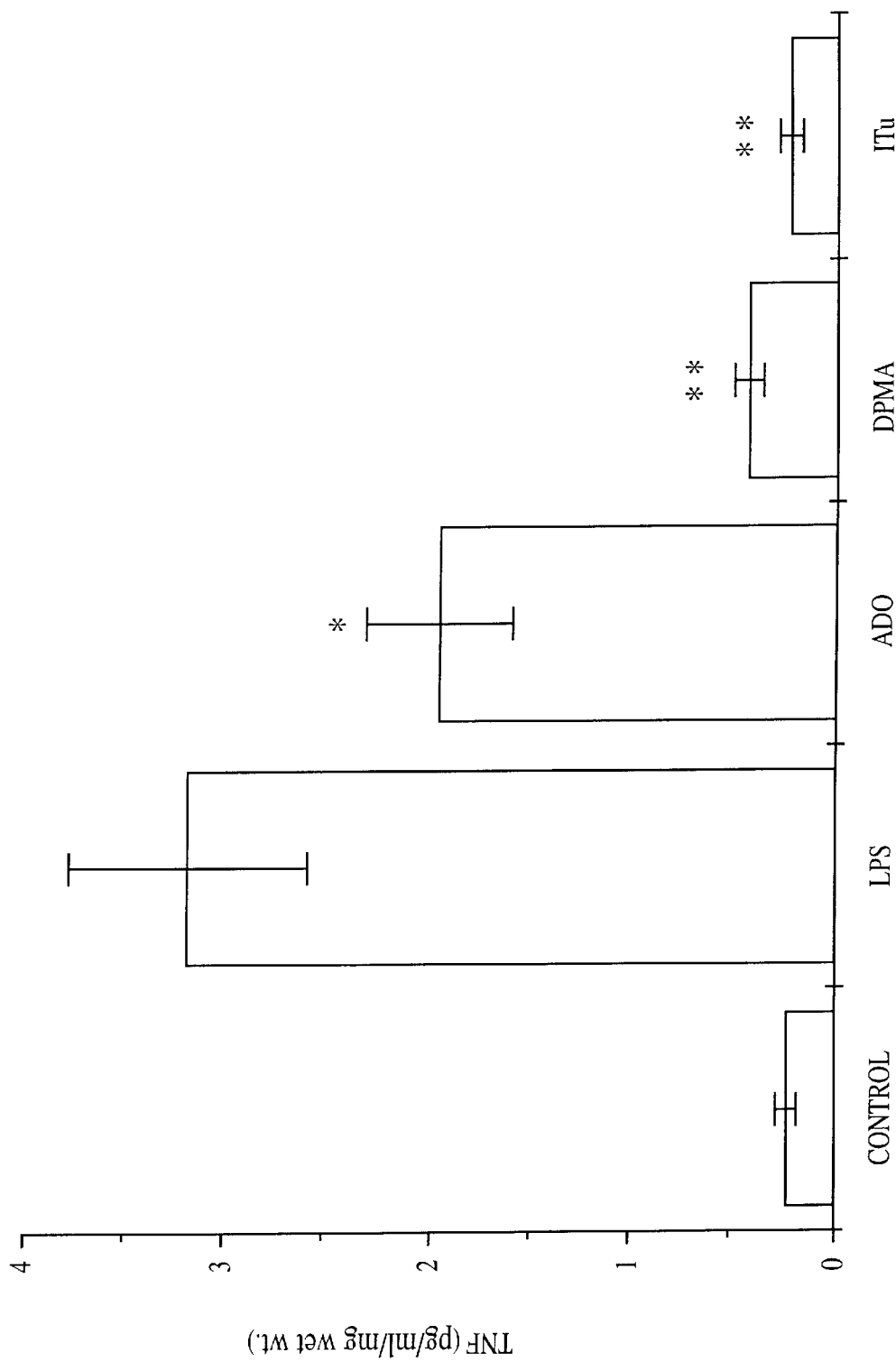
FIG. 14. Effect of adenosine on failing human trabecular muscles. Human heart muscle sections were stimulated with 10 μg/ml LPS (*E. coli* 0127) at time 0. Where indicated, adenosine (ADO) 10 μmol/L, the A agonist DPMA 10 nmol/L or the adenosine kinase inhibitor iodotubercidin (Itu) 10 μmol/L were added at time 0. After 4 hours, supernatants were collected and TNF-α was measured with ELISA. *p<0.05 and **p<0.001 vs. LPS (n=7, ANOVA).

In contrast to healthy rat papillary muscles studied previously, trabecular muscles from failing human hearts released TNF-α in the absence of LPS (0.22±0.05 pg/ml/mg wet weight). Immunohistochemistry confirmed that myocytes were a principal source of TNF-α in the LPS stimulated heart muscle strips. As seen in FIG. 14, adenosine 10 μM decreased TNF-α by 40% ($p<0.05$). The selective adenosine A, receptor agonist DPMA 10 μM decreased TNF-α by 87% ($p<0.001$). Itu, an adenosine regulating agent which increases endogenous adenosine concentration, inhibited TNF-α release by 93 % ($p<0.001$).

The response to LPS challenge was more pronounced for muscle strips obtained from patients with ischemic Cardiomyopathy (5.09−+0.72 pg/ml/mg weight, n=3) than for muscle strips from patients with dilated Cardiomyopathy (1.2±0.29 pg/n-fl/mg weight, n=4) (FIG. 15). The difference was significant ($p<0.001$). There was no significant difference in age (52 vs. 49 years) or difference in medical regimen between both groups. Adenosine had a significant effect ($p<0.005$) on TNF-α release in the ischemic Cardiomyopathy group but did not alter TNF-α release in the dilated Cardiomyopathy group. DPMA and Itu had a significant effect on TNF-α in both groups.

The study above was extended to human heart conditions where it was shown that adenosine inhibits expression of TNF-α in the failing human heart. It extends the prior observation that adenosine inhibits expression of TNF-α in neonatal rat cardiomyocytes, in adult rat cardiomyocytes and in rat papillary muscles. Consistent with the hypothesis that adenosine acts through the myocyte $A_2$ receptor, the selective adenosine $A_2$ receptor agonist DPMA decreased TNF-α by 87% ($p<0.001$). As seen in isolated myocytes and in rat papillary muscles, iodotubercidin markedly reduced TNF-α release by 93% ($p<0.001$). Iodotubercidin increases endogenous adenosine concentration by inhibiting adenosine kinase. It has been shown to decrease TNF-α in a model of septic shock.

Recently, our lab has shown that reducing levels of TNF-α in myocardial tissue does in fact attenuate and may even completely stop progression of maladaptive remodeling of the myocardial tissue (i.e., fibrosis). This was demonstrated by overexpression of solubulizable TNF-α receptors in mice and confirmed by the administration of antibodies specific to TNF-α to mice. By measuring interstitial infiltrates, it was observed that maladaptive remodeling was substantially prevented with both procedures.

IV. A model to study CHF in mammals—Dilated Cardiomyopathy in Transgenic Mice with cardiac specific expression of TNF-α.

1. Construction of the Transgene.

A transgene construct was made containing the murine α-MHC promoter with complementary DNA (cDNA) to murine TNF-α. To generate the plasmid vector, we first used a polymerase chain reaction (PCR)-based approach to amplify a portion of the PG12-Basic plasmid (Promega), which has a multiple cloning site, a firefly luciferase gene, and the SV40T antigen intron and polyadenylation signals (SVpA). Amplification primers 5'-ctt tat gtt ttt ggc gtc ttc ca-3' (complement to nucleotides 77–99) were used to amplify a region of pGL2-Basic which excluded the luciferase coding sequences, and introduced a Hind III site at the 3' end of the amplified DNA. After Hind III digestion, the amplified plasmid was self-ligated to generate a pGL-SVpA vector. Finally, a 5.5-kb Sac I-Sal I fragment of the murine α-MHC promoter (generously provided by Dr. Jeffrey Robins) was isolated and ligated into Sac I-Xho I digested pGL-SVpA to generate pGL-MHC-SVpA.

RAW 264.7 cells treated with lipopolysaccharide for 6 hours were used to generate cDNA to murine TNF-α. The cDNA was amplified with a sense primer (5'-gga gaa cag aaa ctc cag aac atc c-3') corresponding to TNF-α cDNA nucleotide 34 to 58, and an antisense primer (5'-ggg gat ccc caa gcg atc ttt att tct ctc-3') containing a Bam HI site not found in the murine sequence followed by nucleotides complementary to TNF-α cDNA bases 1608 to 1627. TNF-α cDNA was then cloned in the pCR2.1 vector using a TA Clonig Kit (Invitrogen) to create plasmid pCR-TNF-α. The identity of the TNF-α coding sequence was confirmed by sequence analysis (Sequenase Version 2.0 DNA Sequence Kit, USB), pCR-TNF was first digested at the vector Eco RV site, Hind III linkers added, then digested with Hind III to create a clonable end, and with Bam HI to cleave at the Bam HI site introduced in the initial PCR amplification immediately after TNF-α cDNA base 1627. The 1624 bp fragment (containing 7 nucleotides of the Hind III linker, 18 bp of the pCR2.1 vector, TNF-α cDNA nucleotides 34 to 1627, and 5 nucleotides from the PCR introduced Bam HI site) of pCR-TNF was cloned into an 8.4 kb fragment of pGL-MHC-SVpA after a Hind III/partial Bam HI digestion. This digestion removed SVpA from pCL-MHC-SVpA.Bam HI digestion of pGL-MHC-TNF produced a linear 7.1 kb fragment (MHC-TNF) used for microinjection into mouse embryos.

2. Generation and Identification of Transgenic Mice.

FVB mice were used for generation of transgenic animals. Microinjection of the transgene was accomplished in the Transgenic Mouse Facility, University of Pittsburgh. After offspring were born, the tails were biopsied at the age of 10 days. Genomic DNA was isolated using a proteinase K method previously described. Transgenic mice were identified by PCR with a sense primer (5'-cca cat tct tca gga ttc tct-3') specific to the MHC promoter exon 2 and a antisense primer (5'cag cct tgt ccc ttg aag aga-3') specific to the TNF-α cDNA nucleotides 579 to 599 as previously described.

3. Pathological Analysis.

Mice were euthanized under methoxyflurane anesthesia prior to pathological evaluation. All surgical procedures were performed according to the protocols approved by the Institutional Animal Care and Use Committee, University of Pittsburgh. After measurement of body weight, the heart was excised and rinsed in ice-cold 30 mmol/L KCI. Tissues were snap-frozen in liquid nitrogen for RNA and protein analysis, or immediately immersion-fixed in 10% neutral buffered formalin for hematoxylin and eosin (H&E), as well as Masson's trichrome staining. Apoptotic cells were assessed using a commercially available terminal deoxynucleotidyl transferase-medicated dUTP-biotin nick end labeling (TUNEL) kid (ApopTag, Oncor).

4. Northern Blot Analysis.

Total RNA was extracted from frozen tissues by using an acid guanidinium thiocyanate-phenol-chloroform method. The concentration of RNA in each sample was assessed spectrophotometrically. After denatured at 95° C. for five minutes, total RNA (10 μg/lane) was electrophoretically separated in a 0.8% formaldehyde agarose gel, and transferred onto nitrocellulose membrane (Optitran, Schleicher & Schuell) by overnight capillary transfer with 10X SSC. The membrane was then baked at 80° C. for 90 minutes, and prehybridized overnight at 42° C. in 5X Ssc, 50% formamide, 5X Denhardt's reagent, 0.2% SDS and 25 mmol/L sodium phosphate. A.1.1 kb Eco RI fragment of the transgene was used as a hybridizationprobe to detect transgene transcripts, which should be 1.7 kb long if correctly spliced. The probe was radiolabeled with [αP]dCTP (3000 Ci/mmol DuPont) using a Random Primed DNA Labeling Kit (Boehringer Mannheim), and then hybridized to the membrane overnight at 42° C. The membrane was subsequently washed 4 times with 2X SSC.0.1% SDS at room temperature, followed by two washes with 0.3X SSC, 0.1% SDS at 55° C. and exposed to a PhosphorImager cassette (Moecular Dynamics).

5. Reverse Transcriptase Polymerase Chain Reaction (RT-PCR).

First-strand cDNA was synthesized by reverse transcription of 1 μg of total RNA by using oligo-dT primers according to manufacturer's instructions (SuperScript II, Gibco BRL). Primers specific to the MHC promoter exon 1 (5'-tca gag att tct cca acc cag-3') and complementary to the TNF-α cDNA 579 to 599 (5'-cag cct tgt ccc ttg aag aga-3') were used to detect the transgene transcripts as previously described.

6. Enzyme-Linked ImmunoSorbent Assay (ELISA).

Tissue levels of TNF-α protein were assessed using a commercially available ELISA kit for mouse TNF-α (Factor-Test-X, Genzyme), as previously reported. Frozen tissues (5 to 20 mg) were homogenized in 300 to 500 μL ice-cold phosphate-buffered saline containing 1 mmol/L phenylmethylsulfonyl Fluoride protease inhibitor (Sigma). After brief centrifugation, samples were kept on ice for the duration of the assay. Total protein levels were quantitated using a commercially available assay (Bio-Rad Protein Assay, Bio-Rad Laboratories) with bovine serum albumin (Sigma) as a standard (0 to 2 mg/mL). Tissue samples were standardized to 20 μg total protein in 100 μL diluent buffer for each immunoassay. Mouse TNF-α provided by the manufacturer was used as a standard (0 to 2240 pg/mL). All assays were done in duplicate. Results were analyzed spectrophotometrically at a wavelength of 450 nm with a microliter plate reader. TNF-α values are reported as pg/mL of standardized sample (equivalent to pg/200/μg total protein).

7. Magnetic Resonance Imaging (MRI).

Female transgenic mice and wild type controls at the ages of 9 and 24 weeks were studied. Images were acquired on a Bruker Avance 7T spectrometer using a home-built single loop RF coil. to anesthetize the mice, sodium pentobarbital was applied intraperitoneally in two doses: the first dose was 0.06 mg/g body weight and 20 minutes later a second dose of 0.04 mg/g body weight was applied. After sedation, the mouse was placed prone on the coil, with the heart positioned above the coil center. Image acquisition was gated to both the respiratory and cardiac cycles. A pilot coronal image was obtained from which the long axis of the heart was identified. Eight oblique transverse slices, with a slice thickness of 1 mm and an interslice gap of 0.2 mm, provided short axis images through the heart, covering the entire left ventricle. The acquisition order of the multislice set was rotated so that every slice was obtained at eight different time points, allowing for images to be obtained from end-diastole, through systole, and into mid-diastole. Diffusion gradients were used to crush the signal from flowing blood. The left ventricular volume was estimated by tracing the left ventricular endocardial border and then multiplying by the slice thickness of 1.2 mm. A previous study demonstrated that there was a high degree of correlation between MRI estimated ventricular mass and autopsy measurements (r=0.996).

8. Left Ventricular Pressure Measurement.

Five 12-week-old and seven 24-week-old transgenic mice, and five 12-week-old and five 24-week-old wild type controls were studied. The mice were female except three transgenic and two wild type at 12 weeks of age. After anesthetized with 2.5% Avertini (18 μL/g body weight ip), mice were placed in a supine position, and surgically intubated with a modified 20 gauge needle connected to a volume-cycled rodent ventilator (Harvard Apparatus) with a tidal volume of 0.2 to 0.4 ml and respiratory rate of 110 per minute. The chest was opened, and a 1.4 F micromanometer catheter (Millar Instruments) was inserted into the left ventricle through the apex. Left ventricular pressure, was recorded at the baseline and two minutes after low and high doses of isoproterenol injection (0.1 and 1 μg ip). All data was digitized at 1 kHz and stored on a customized personal computer for subsequent analysis.

9. Statistical Analysis.

All statistical analysis were performed using SPSS software (SPSS). The results are presented as mean±SD unless mentioned otherwise. Student's t test was used to compare each variable between transgenic mice and age-matched controls. Mann-Whitney rank-sum test was used to compare mice that had died spontaneously with mice that were intentionally sacrificed, because those that died spontaneously had a significantly larger variance as a group. ANOVA with or without repeated measures were used when more than two groups were compared. Mortality rate was estimated by Kaplan-Meier survival analysis. Differences were considered significant at a value of $p<0.05$.

10. Generation of Transgenic Mice.

The transgene construct was microinjected into the pronuclei of one-cell mouse embryos after which the embryos were surgically reimplanted into pseudopregnant mice. Screening of the offspring by PCR identified three potential founders harboring the TNF-α transgene, all of which were grossly indistinguishable from non-transgenic littermates. One mouse was male but produced no offspring despite mating with several females. A second mouse was female and delivered 79 offspring in six litters. However, only one of them, which died at three days of age, carried the transgene. This founder died at 44 weeks of age and a subsequent autopsy demonstrated pathology consistent with heart failure including ventricular dilatation and pulmonary edema. The third mouse was also female and produced a number of offspring harboring the TNF-α transgene. This founder also developed subsequent congestive heart failure at 50 weeks of age and died with a profoundly dilated heart. The TNF-α transgene appeared to be X-linked as only female mice harbored the transgene when transgenic males were outcrossed with wild type females. Furthermore, when transgenic females were outcrossed with wild type males, both males and females harbored the transgene.

Figure 16:
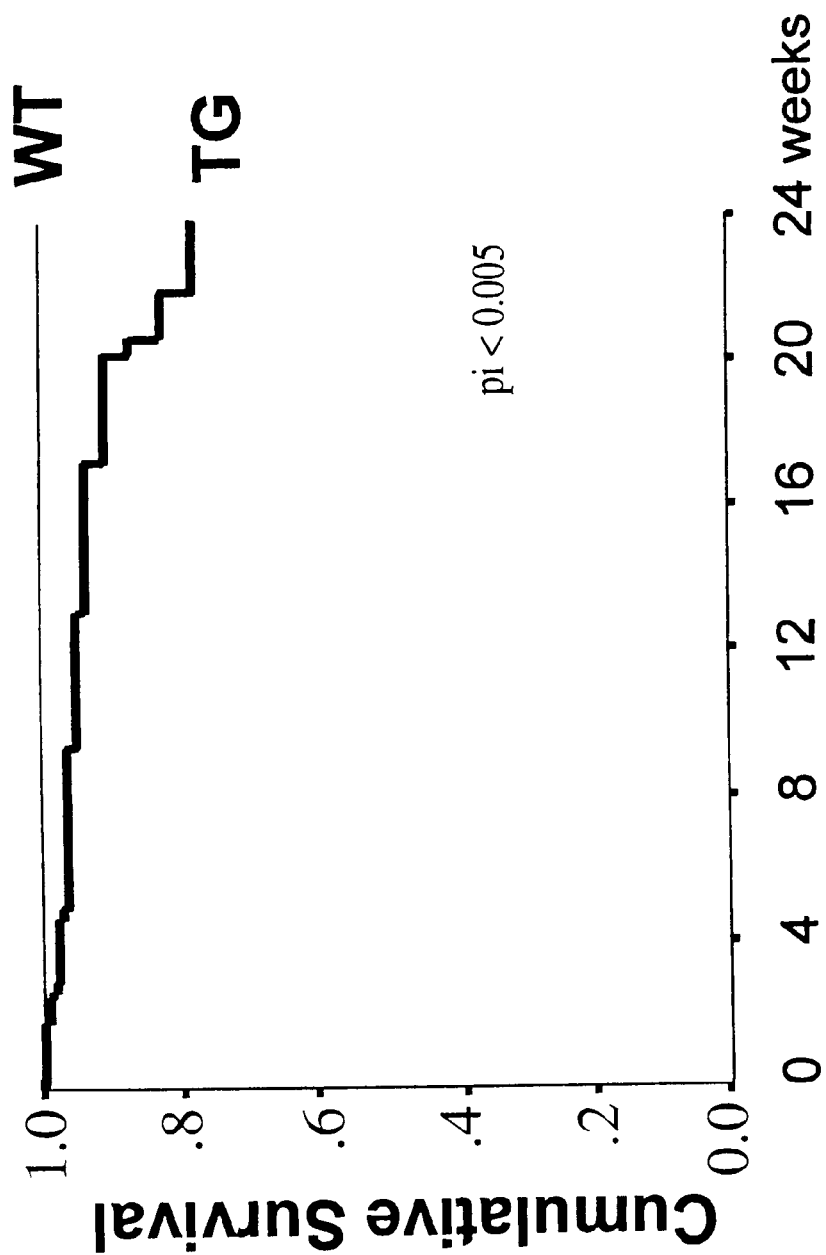
FIG. 16. Survival function curves from transgenic mice (TG, n=176) and wild type littermates (WT.n=195). TG had significantly lower survival (p<0.005) and the cumulative mortality rate at six months was 23%.

After the screening at 10 days, 15 of 176 transgenic mice-were found to have died spontaneously. This was in marked contrast to an absence of death in wild type littermates (n=195). As seen in FIG. 16, the survival rate for the transgenic mice was substantially different from that of littermate controls with the mean time to death being 297±17 (SE) days (p<0.005). Although there were no statistical differences in mortality between transgenic males and females, the generations of mice had significant effects on mean survival time (F0 - 351 days, F1 - 209±25 days, F2=160±2 days, F3=86+2 days, p<0.05). Subsequent autopsies suggested that at least 11 of the 15 deaths were associated with congestive heart failure.

11. Expression of TNF-α Transgene and Protein in the Heart.

Figure 17:
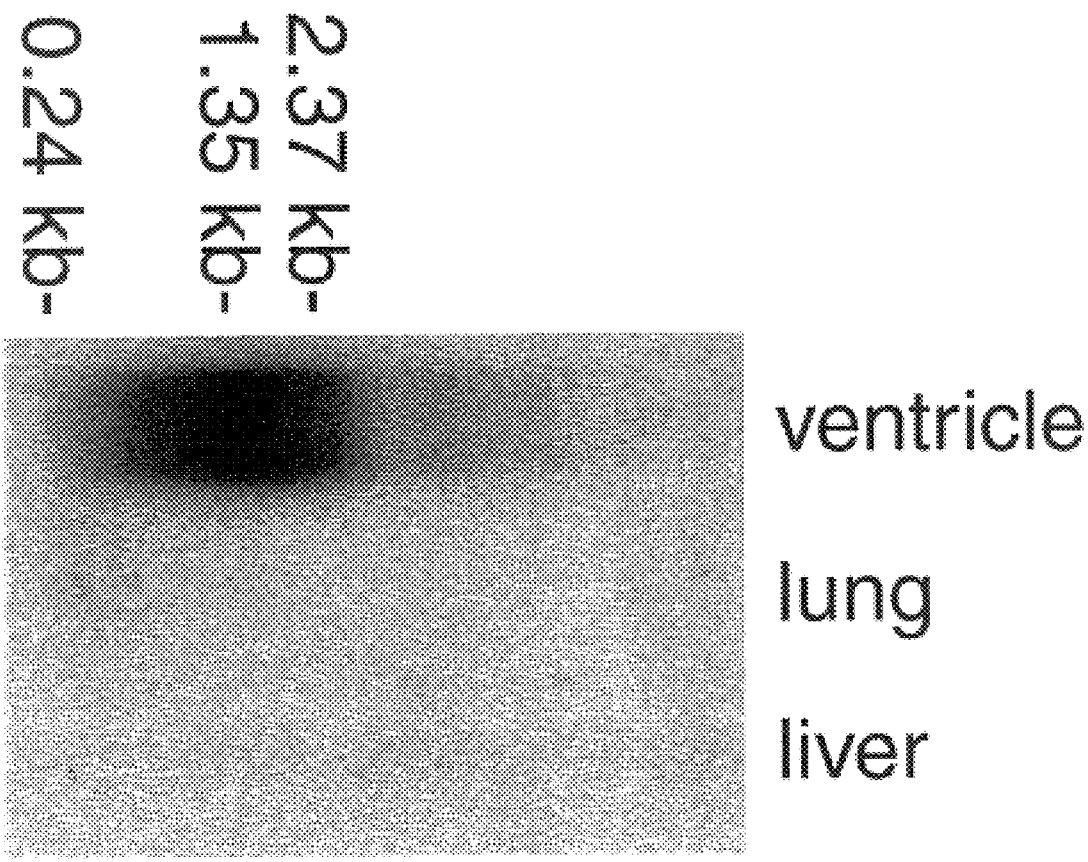
FIG. 17. Northern blot analysis for the transgene transcripts. Total RNA was extracted from ventricle, lung, and liver in a 12-week-old transgenic mouse. The transgene was expressed in the ventricle but not in the lung or in the liver.

A group of transgenic mice and wild type controls were sacrificed for analysis at the age of 6, 12 and 24 weeks. Transgene expression was assessed using Northern blot analysis of total RNA from various tissues including heart, lung, and liver. Robust expression of the transgene was found in the heart; however, no transgene expression was noted in either the liver or the lung (FIG. 17). RT-PCR detected multiple bands for the TNF-α transgene, consistent with our earlier observation of the presence of multiple slice variations of the TNF-α transgene.

Figure 18:
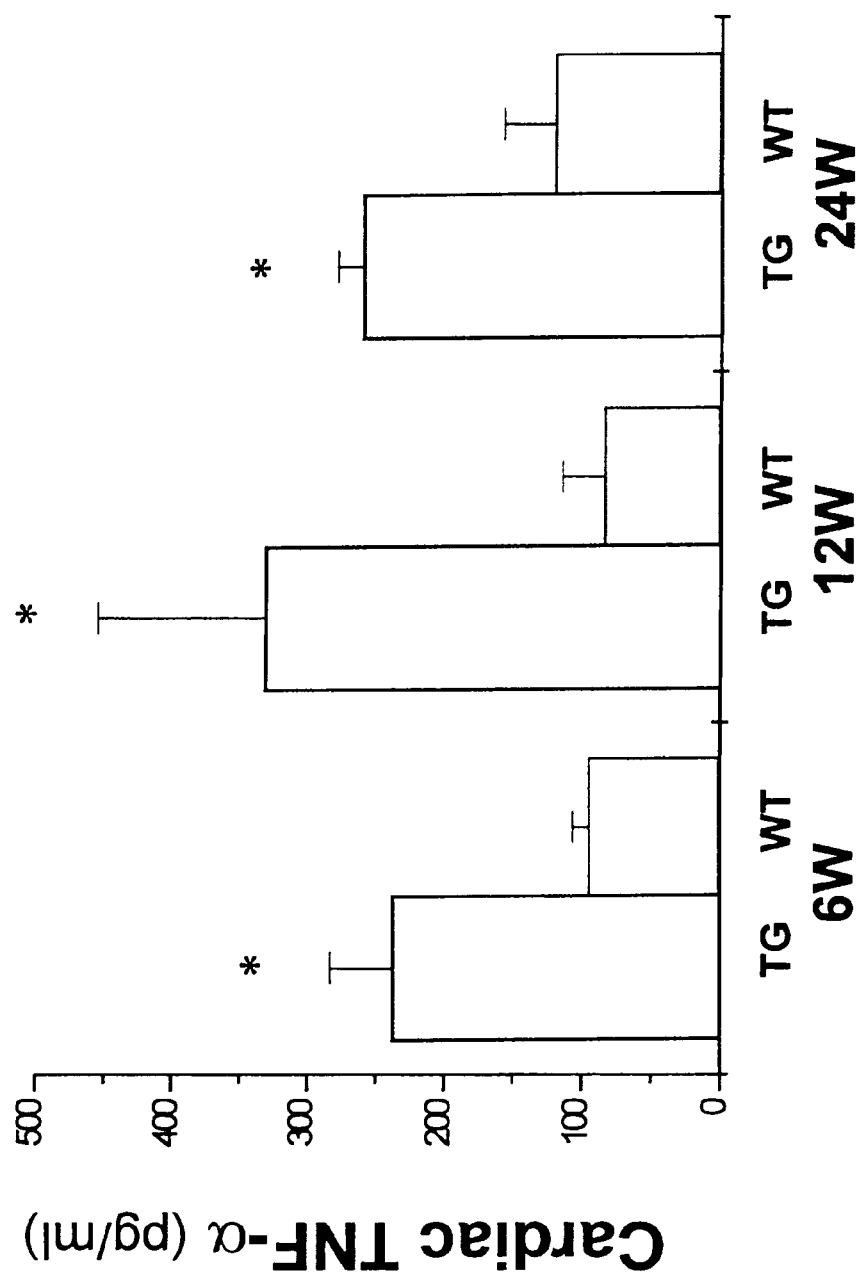
FIG. 18. TNF-α protein levels in the ventricle by ELISA. Transgenic mice (TG) and wild type controls (WT) were analyzed at the age of 6, 12, and 24 weeks. Values are expressed as mean+SD. TNF-α levels were significantly higher in TG at all ages (*p<0.001 vs WT). There were no significant differences among ages.
Figure 19A:
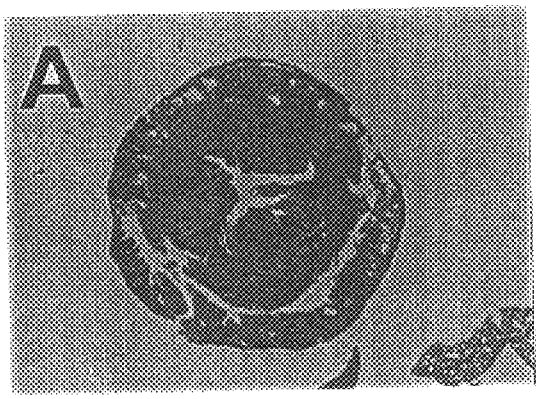
FIG. 19. H&E staining (A, D, G; 5X), Trichrome staining (B, E, H; 20X) and TUNEL assay (C, F, I; 200X) of the heart. Panels A, B, and C represent a 24-week-old wild type control; Panels D, E, and F, a 24-week-old transgenic animal; Panels G, H, and I, a mouse that died spontaneously at the age of 20 weeks. In the heart harboring the transgene, eccentric hypertrophy (Panel D), patchy interstitial fibrosis (Panel E), and interstitial inflammation (Panel F) were observed. A large arrow in Panel F indicates myocyte multinucleation, and small arrows show apoptosis in the interstitial cells. The mouse that died spontaneously developed marked biventricular dilatation (Panel G). An arrow in Panel I shows an apoptotic cardiomyocyte.
Figure 19B:
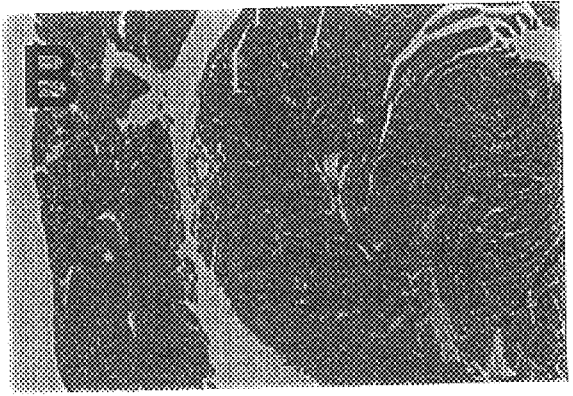
Figure 19C:
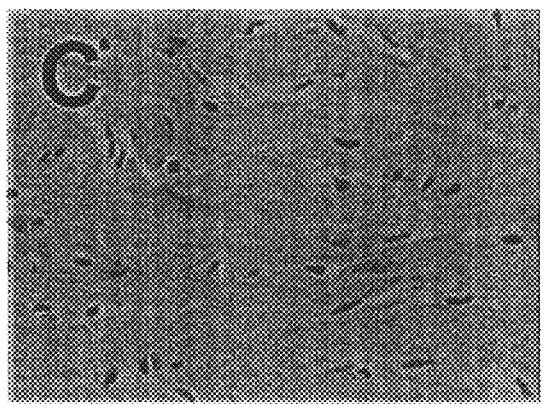
Figure 19D:
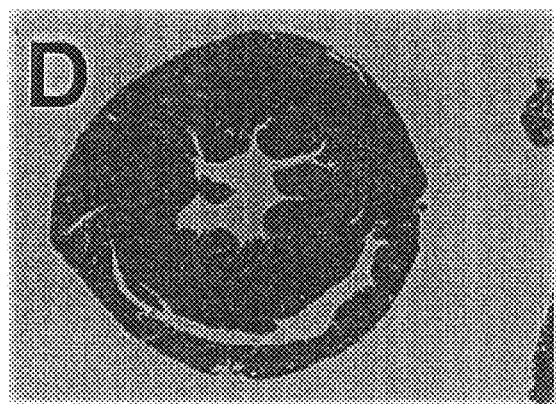
Figure 19E:
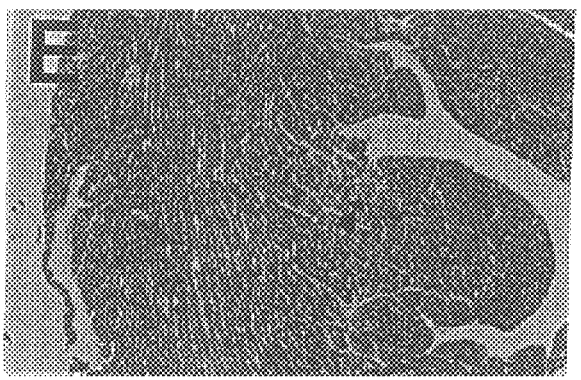
Figure 19F:
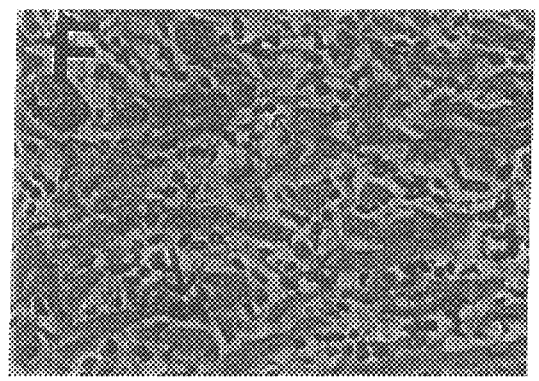
Figure 19G:
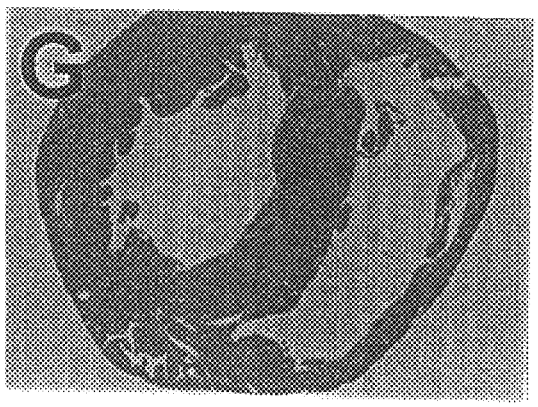
Figure 19H:
Figure 19I:
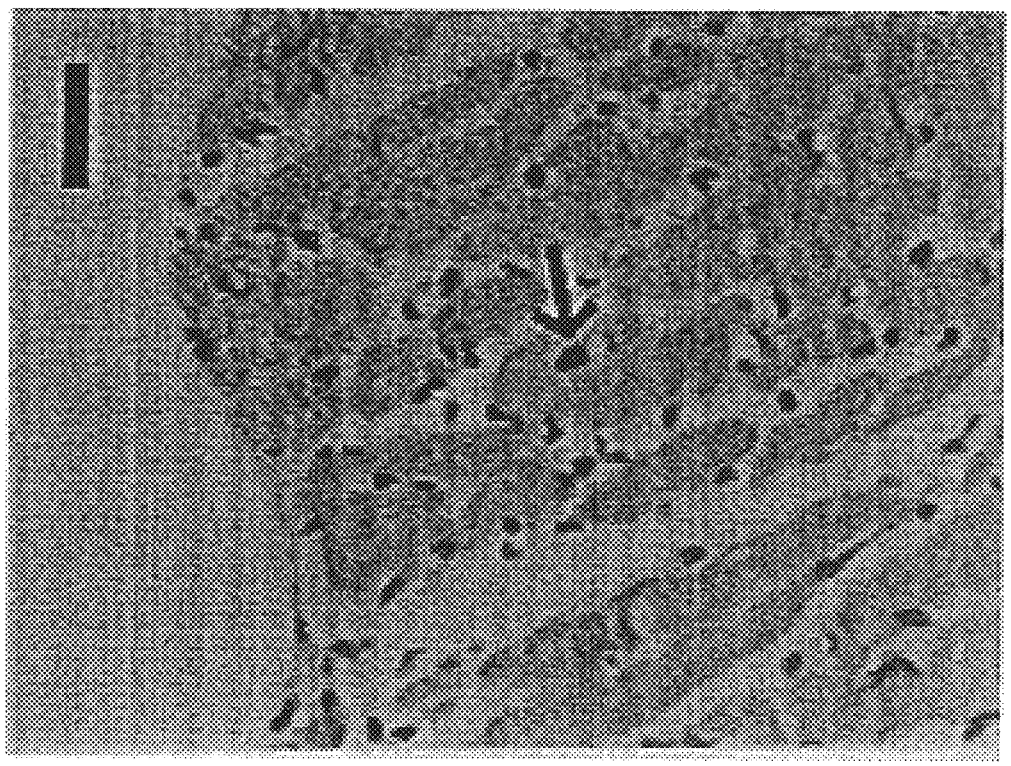
Figure 20A:
FIG. 20. Representative MR images from a 24-week-old transgenic mouse (A, B, C) and an age-matched wild-type control (D, E, F). Panels A and D illustrate coronal views of the mice; B and E, short axis views of the heart in end-diastole; C and F, in end-systole. White scales indicate 2.5 mm. The transgenic heart was dilated with reduced ejection fraction (50%).
Figure 20B:
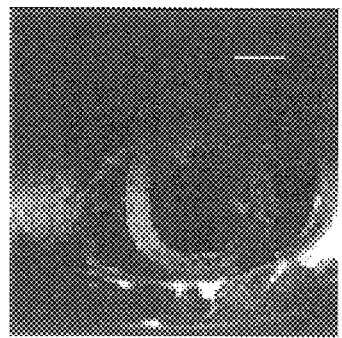
Figure 20C:
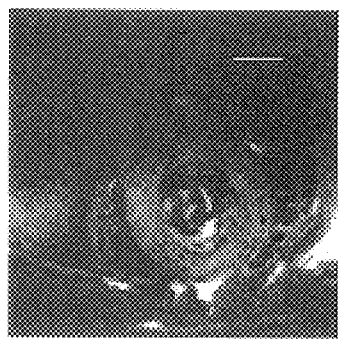
Figure 20D:
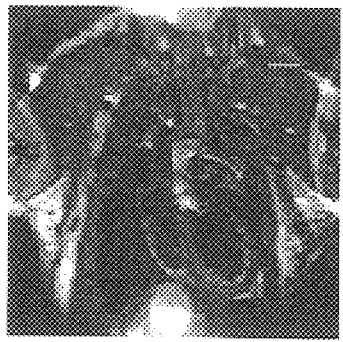
Figure 20E:
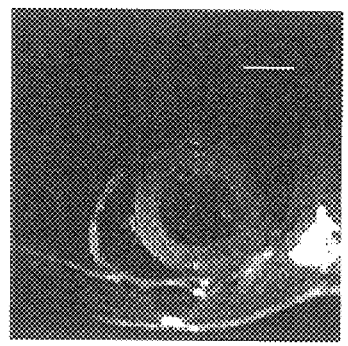
Figure 20F:

FIG. 18 shows cardiac TNF-α levels by ELISA in transgenic mice and wild type controls at each age. TNF-α levels were significantly higher in the transgenic mice than in littermate controls (p<0.001). However, age did not appear to influence TNF-α levels as there was virtually no difference in levels among 6, 12, and 24 weeks. Similarly, gender had no effects on TNF-α levels as 12 week-old males (269±70 pg/mL, n=3) and females 361±138 pg/ml, n=6) had similar levels of TNF-α. In addition, TNF-α levels in mice that died spontaneously (243±94 pg/mL) were similar to those in the sacrificed transgenic mice. However, we cannot exclude the possibility that proteolysis decreased the levels of TNF-α in the carcasses. Cardiac levels of TNF-α in transgenic mice of the present study were approximately an order of magnitude less than those found in the heart of a mouse expressing the TNF-α transgene in which the 3' destabilizing region had been deleted (1483 pg/ml). Immunoreactive TNF-α levels in either lung, liver or sera were not different between 12-week-old transgenic mice and wild type controls (FIG. 22), consistent with the Northern blot analysis demonstrating that the transgene transcripts were limited to the heart.

12. Gross Pathology and Histology.

Gross pathological observation of the hearts harboring the transgene suggested the presence of cardiac enlargement. This finding was confirmed by the presence of an elevation in heart weight/body weight ratios as early as six weeks of age (FIG. 23). An elevation in heart weight was also recognized in these animals.

This histology of the transgenic animals was easily distinguishable from age-matched controls in all ages (6, 12, and 24 weeks), and an evolution of histopathological changes developed over time. Representative images are presented in FIG. 19. Changes in the interstitium were obvious by routine light microscopy. There was an increase and hypertrophy of interstitial cells, which appeared to consist mostly of histiocytes, fewer lymphocytes and hypertrophied interstitial connective tissue cells. Apoptotic cell death in this population was evident both by routine light microscopy and by the TUNEL assay. There was also mild interstitial edema, an apparent increase in the production of matrix material and focal interstitial changes were associated with mild myocyte hypertrophy, and focal myocyte degeneration in the form of rate areas of single cell dropout and occasional myocyte multinucleation. Apoptotic myocytes were present but rarely seen.

Autopsies were also performed with 16 transgenic mice, including two founders, which died spontaneously during the study period. Both ventricles and atria were extremely enlarged in these animals, and lung weight was also increased (FIG. 17). Pleural effusions with or without ascites were present in nine, and organized thrombi were observed in six out of 16 atria. Exceptional dilatation of the heart accompanied by increased lung weight and pleural effusion suggested that most of these animals (at least 12 of 16) died because of congestive heart failure.

The histopathological changes in the interstitium were qualitatively similar to those seen in the sacrificed transgenic mice, but in several of the animals that was a noticeable increase in the lymphocytic component of the interstitial cells. This was associated with more clearly recognizable myocyte injury, myocyte and interstitial cell multinucleation, and rare but definite, myocyte apoptosis. The interstitial fibrosis was relatively severe in some of the animals but overall, interstitial fibrosis was not an overriding feature. The endocardium and pericardium were slightly fibrotic, but there was no evidence of significant pathological change in the intramyocardial branches of the coronary arteries.

13. Cardiac Function.

Because of its small size and rapid heart rate, functional analysis of transgenic myocardium has been challenging. In particular, sensitive measures of in vivo cardiac function have been technically difficult. However, recent advances in MRI technology have provided the capability to evaluate cardiac mass and function in the anesthetized mouse. Representative MR images from a 24 week-old transgenic mouse and an age-matched wild type control are shown in FIG. 20. The coronal view image of the transgenic mouse clearly demonstrated that the heart was dilated and globoid-shaped. Left ventricular volume was estimated by tracing the intraventricular area in five consecutive short axis images where each slice was 1.2 mm thick. The end-diastolic and end-systolic volumes were 0.104 mL and 0.052 mL in the transgenic mouse (ejection fraction=50%), and 0.064 mL. and 0..018 ml, in the wild type control (ejection fraction=72%). Cumulative data, presented in FIG. 24, demonstrated a progressive increase in end-diastolic and end-systolic volumes with age in mice overexpressing TNF-α. As a result, left ventricular ejection fraction was significantly decreased at 24 weeks of age ($p<0.0\,1$).

Figure 21:
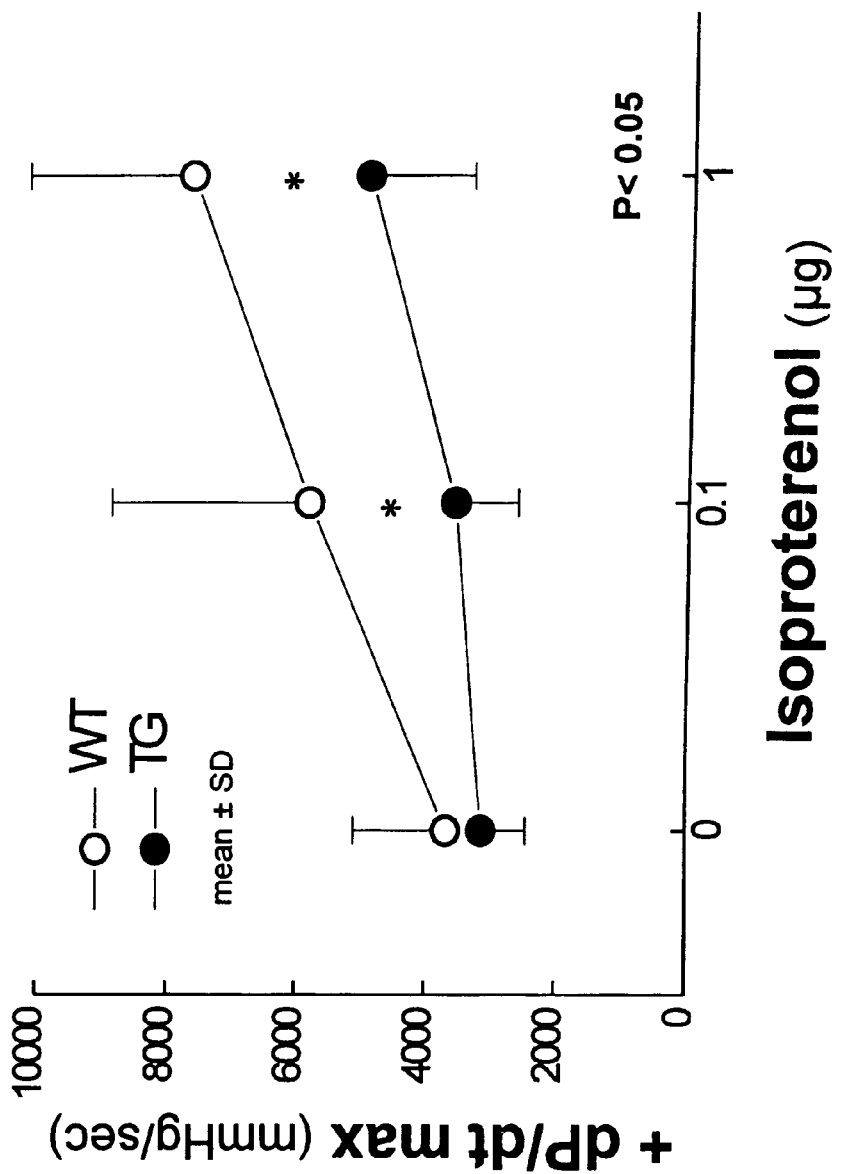
FIG. 21. Left ventricular dP/dtmax before and after isoproterenol injections in transgenic mice (TG) and wild-type controls (WT). Values are mean±SD. Left ventricular dP/dtmax was significantly lower in TC (p<0.05), and it did not respond to isoproterenol as much as WT (p<0.005).

Left ventricular pressure was measured in 12 transgenic and 10 wild type mice at 12 or 24 weeks of age. Because neither age nor gender had a significant effect on hemodynamic parameters, results are summarized as a whole. There were no significant differences in heart rate or systolic blood pressure between the transgenic mice (342±37 bpm, 56±9 mmHG) and the wilds type controls (364±49 bpm, 66±15 mmHg). After 0.1 and 1 µg isoproterenol injection, heart rate was increased in the transgenic mice as well as in the controls (113±16% vs 111±15%, and 137±20% vs 135±20%). Blood pressure was not significantly changed after isoproterenol injections in both animals. We used left ventricular $dP/dt_{max}$ was an index of contractility. As shown in FIG. 21, left ventricular $dP/dt_{max}$ was significantly lower in the transgenic mice ($p<0.05$). Additionally, the response to isoproterenol was attenuated in the transgenic animals ($p<0.005$). In eight mice, we had also performed MRI on the day preceding the pressure measurement. There was a significant correlation between the $dP/dt_{max}$ at baseline and the ejection fraction estimated by MRI in these animals (r-0.73, $p<0.05$). Our transgenic mice showed early expression of IL-1B and IL-6, confirming the finding that TNF-α can initiate the downstream cytokine cascade.

That end stage congestive heart failure is associated with a marked increase in circulating TNF-α levels has been reported by numerous investigators. Furthermore, these appears to be a direct relationship between disease severity and circulating levels of TNF-α. Additionally, recent studies have demonstrated that although the non-failing heart does not express TNF-α, the failing myocardium expresses abundant amounts of this proinflammatory cytokine. Whereas initial reports suggested that TNF-α was expressed by inflammatory cells within the myocardium, it is now clear that myocytes themselves can express TNF-α o at times of stress. However, the precise role of TNF-α in the pathophysiology of congestive failure and/or the transition from compensated to decompensated heart failure remains unclear, Similarly, studies have not defined whether these changes in cardiac TNF-α expression are pathophysiologically important or simply an epiphenomenon associated with end-stage heart failure.

In this report, we demonstrate that chronic overexpression of TNF-α results in the development of a dilated cardiomyopathy that is phenotypically indistinguishable from congestive failure due to idiopathic dilated cardiomyopathy. In contrast to wild type controls, the animals overexpressing TNF-α demonstrated: 1) ventricular hypertrophy; 2) ventricular dilatation; 3) interstitial infilgrates; 4) interstitial fibrosis; 5) rare myocyte apoptosis; and 6) a substantial decrease in left ventricular contractile performance. Additionally, mice overexpressing the TNF-α transgene had a marked increase in mortality. More than half of spontaneously died mice presented exceptional dilatation of the heart, increased lung weight, and pleural effusion, suggesting that they died of congestive heart failure.

In an earlier report, we demonstrated that robust overexpression of TNF-α in a mouse resulted in the development of a lethal myocarditis before the completion of weaning. By contrast, the mice in the present report demonstrated levels of TNF-α that were approximately an order of magnitude less than those reported in the mouse with lethal myocarditis. It is unlikely that this disparity could be attributed to the analysis of tissue from a carcass in the earlier study, but analysis of tissue obtained fresh from randomly sacrificed animals in the p resent study. Myocardial TNF-α levels from the carcasses of mice that died spontaneously in the present study were similar to those in the animals that were randomly sacrificed. Rather, it would appear that the destabilizing region in the 3' tail of the TNF-α gene plays an important part in regulating TNF-α expression.

Although only a single transgenic line was established in this study, three potential founders were produced and two of them died of congestive heart failure. The gross pathology and histology were indistinguishable between these two animals. Therefore, the development of the phenotype cannot be attributed to the site of genomic integration. Transgenic progeny demonstrated phenotypic heterogeneity, as survival was considerably different among different mice and TNF-α levels did not appear to reflect prognosis. However, this finding was not surprising as clinical heterogeneity is a hallmark in patients with heart failure as well as in patients with genetically linked heart muscle disease.

The measurement of cardiac mass and function in the mouse is technically challenging because of the small size of the heart and its rapid rate. In the present study, we have taken advantage of the recent adaptation of MRI technology to non-invasively assess cardiac structure and function in the mouse. MRI is able to provide simultaneous measures of morphology and function by gating the image acquisition to both the electrocardiogram and the respiratory signal, thereby abrogating motion artifacts and ensuring that images are obtained at specific points through the cardiac cycle. Furthermore, multiple image slices in MRI can be obtained in the same amount of time required for a single slice. This permits acquisition of eight short axis slices at many different points through the cardiac cycle in a decreased amount of time. A previous study has demonstrated the ability of MRI to detect relatively small changes in cardiac mass secondary to catecholamine induced hypertrophy. The results of that study indicate a high degree of correlation between MRI estimated heart mass and autopsy measurements. In the present study, we demonstrate the usefulness of MRI in evaluating left ventricular hypertrophy, cavity dilatation, and function in the TNF-α transgenic mice in comparison with wild type controls. It is not surprising that the development of cardiac dilatation in the transgenic mouse occurs over a period of six months and that hypertrophy and fibrosis appear to precede dilatation and diminished pump function. Indeed, it has been proposed that hypertrophy, myocyte loss, and interstitial fibrosis are early components of the transition from compensated to decompensated myocardium.

The present study strongly suggests an important pathophysiologic role for TNF-α in the pathogenesis of end-stage heart failure. The TNF-α transgenic mice develop a primary phenotype fully consistent with congestive heart failure, displaying both cardiac dilatation and left ventricular dysfunction. Therefore it should provide an excellent tool with which to analyze physiological and biochemical changes that accompany the transition from compensated to decompensated myocardium and the development of end-stage heart failure. Additionally, the opportunity to modify or rescue the heart failure phenotype by directed cross-breeding with mice harboring selected gene mutations will facilitate an understanding of the mechanisms which compensate or progress cardiac dysfunction. Similarly, the TNF-α overexpression model may provide an unique platform for preclinical evaluation of gene transfer or pharmacological therapy.

Although the invention has been described in terms of particular embodiments in an application, one of ordinary skill in the art, in light of this teaching, can generate additional embodiments and modifications without departing from the spirit of, or exceeding the scope of the claimed invention. Accordingly it is to be understood that the drawings and the descriptions herein are proffered by way of example only to facilitate comprehension of the invention and should not be construed to limit the scope thereof.

What is claimed is:

1. A method of preventing remodeling of myocardial tissue in a mammal, comprising increasing cellular availability of adenosine.

2. The method of claim 1, wherein said mammal is a human.

3. The method of claim 2, wherein said step of increasing cellular availability of adenosine includes administering therapeutically effective amounts of adenosine.

4. The method of claim 2, wherein said step of increasing cellular availability of adenosine includes administering biological equivalent of adenosine.

5. The method of claim 3, wherein said adenosine is administered intravenously.

6. The method of claim 2, wherein said step of increasing cellular availability of adenosine includes administering a compound from the group consisting of an adenosine $A_2$ receptor agonist, an adenosine transport inhibitor, an adenosine deaminase inhibitor, and an adenosine kinase inhibitor.

7. The method of claim 6, wherein said compound is administered orally.

8. The method of claim 2, wherein said remodeling is maladaptive remodeling of the myocardial tissue.

9. The method of claim 8, wherein said maladaptive remodeling is indicated detected as a symptom of congestive heart failure.

10. A method of preventing degradation of myocardial tissue associated with end-stage heart disease in a mammal comprising administering therapeutically effective amounts of an adenosine analog.

11. The method of claim 10, wherein said mammal is a human.

12. The method of claim 11, wherein said adenosine analog is an agent which increases cellular availability of adenosine.

13. The method of claim 12, wherein said adenosine analog is erogenous adenosine.

14. The method of claim 12, wherein said adenosine analog is a biological equivalent of adenosine.

15. The method of claim 13, wherein said adenosine is administered intravenously.

16. The method of claim 12, wherein said adenosine analog is a compound from the group consisting of an adenosine $A_2$ receptor against, an adenosine transport inhibitor, an adenosine deaminase inhibitor, and an adenosine kinase inhibitor.

17. The method of claim 16, wherein said compound is administered orally.

18. The method of claim 12, wherein said adenosine analog is selected from the group consisting of dipyridamole and iodotulercidin.

19. A method of treating a patient presenting symptoms of congestive heart failure comprising:

identifying symptoms of the patient indicative of damage to myocardial tissue;

administering an agent which decreases the production of TNF-α in the myocardial tissue.

20. The method of claim 19, wherein said symptoms are indicative of acute myocardial failure, and wherein said agent which decreases the production of TNF-α in the myocardial tissue is comprised of a therapeutically effective amount of adenosine.

21. The method of claim 20, wherein said symptoms are indicative of chronic myocardial failure, and wherein said agent which decreases the production of TNF-α in the myocardial tissue is selected from the group consisting of a biological equivalent of adenosine, an adenosine $A_2$ receptor agonist, an adenosine transport inhibitor, an adenosine deaminase inhibitor, and an adenosine kinase inhibitor.

22. The method of claim 21, wherein said compound is administered orally.

23. A method of increasing clinical end-points in a patient having diseased myocardial tissue comprising administrating an agent which increases cellular availability of adenosine.

24. The method of claim 23, wherein said mammal is a human.

25. The method of claim 24, wherein said step of increasing cellular availability of adenosine includes administering therapeutically effective amounts of adenosine.

26. The method of claim 24, wherein said step of increasing cellular availability of adenosine includes administering biological equivalent of adenosine.

27. the method of claim 25, wherein said adenosine is administered intravenously.

28. The method of claim 24, wherein said step of increasing cellular availability of adenosine includes administering a compound from the group consisting of an adenosine $A_2$ receptor against, an adenosine transport inhibitor, an adenosine deaminase inhibitor, and an adenosine kinase inhibitor.

29. The method of claim 28, wherein said compound is administered orally.

30. The method of claim 24, wherein said remodeling is maladaptive remodeling of the myocardial tissue.

31. The method of claim 30, wherein said maladaptive remodeling is indicated detected as a symptom of congestive heart failure.

32. A method for treating a patient comprising:
   identifying a phenotype in said patient indicative of myocardial formation of TNF-α;
   determining levels of TNF-α in said patient
   administering effective amounts of an agent to decreases the levels of TNF-α in said patient.

33. The method of claim 32, wherein said phenotype is indicative of acute myocardial failure, and wherein said agent which decreases the levels of TNF-α in the patient is comprised of a therapeutically effective amount of adenosine.

34. The method of claim 32, wherein said phenotype is indicative of chronic myocardial failure, and wherein said agent which decreases the levels of TNF-α in the patient is selected from the group consisting of a biological equivalent of adenosine, an adenosine $A_2$ receptor agonist, an adenosine transport inhibitor, an adenosine deaminase inhibitor, and an adenosine kinase inhibitor.

35. The method of claim 34, wherein said compound is administered orally.

* * * * *